(12) United States Patent
Smith et al.

(10) Patent No.: US 10,048,127 B2
(45) Date of Patent: *Aug. 14, 2018

(54) OPTICAL FILTER AND SPECTROMETER

(71) Applicant: Viavi Solutions Inc., Milpitas, CA (US)

(72) Inventors: Paula Smith, Santa Rosa, CA (US);
Curtis R. Hruska, Cloverdale, CA (US); Benjamin F. Catching, Santa Rosa, CA (US); Paul G. Coombs, Santa Rosa, CA (US)

(73) Assignee: VIAVI Solutions Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/818,986

(22) Filed: Aug. 5, 2015

(65) Prior Publication Data
US 2017/0038255 A1    Feb. 9, 2017

(51) Int. Cl.
*G01J 3/28*    (2006.01)
*G02B 5/28*    (2006.01)
(Continued)

(52) U.S. Cl.
CPC ............ *G01J 3/0229* (2013.01); *G01J 3/0205* (2013.01); *G01J 3/0208* (2013.01); *G01J 3/0216* (2013.01); *G01J 3/0218* (2013.01); *G01J 3/0262* (2013.01); *G01J 3/12* (2013.01); *G01J 3/26* (2013.01); *G01J 3/2803* (2013.01); *G01N 21/255* (2013.01); *G01N 21/8507* (2013.01); *G02B 5/22* (2013.01); *G02B 5/3025* (2013.01);
(Continued)

(58) Field of Classification Search
None
See application file for complete search history.

(56) References Cited

U.S. PATENT DOCUMENTS 4,389,096 A    6/1983    Hori et al.
4,590,466 A    5/1986    Wiklund et al.
(Continued)

FOREIGN PATENT DOCUMENTS

CN    101900905    12/2010
CN    102944305    2/2013
(Continued)

OTHER PUBLICATIONS

Partial European Search Report corresponding to EP 16 18 2550, dated Jan. 2, 2017, 8 pages.
(Continued)

*Primary Examiner* — Shawn DeCenzo
(74) *Attorney, Agent, or Firm* — Harrity & Harrity, LLP

(57) ABSTRACT

An optical assembly is disclosed including two laterally variable bandpass optical filters stacked at a fixed distance from each other, so that the upstream filter functions as a spatial filter for the downstream filter. The lateral displacement may cause a suppression of the oblique beam when transmission passbands at impinging locations of the oblique beam onto the upstream and downstream filters do not overlap. A photodetector array may be disposed downstream of the downstream filter. The optical assembly may be coupled via a variety of optical conduits or optical fibers for spectroscopic measurements of a flowing sample.

32 Claims, 20 Drawing Sheets

(51) Int. Cl.
*G01J 3/26* (2006.01)
*G01J 3/02* (2006.01)
*G01J 3/12* (2006.01)
*G01N 21/25* (2006.01)
*G02B 5/22* (2006.01)
*G02B 5/30* (2006.01)
*G02B 6/42* (2006.01)
*G01N 21/85* (2006.01)

(52) U.S. Cl.
CPC ...... *G02B 6/4215* (2013.01); *G01J 2003/123* (2013.01); *G01J 2003/1213* (2013.01); *G01J 2003/1217* (2013.01); *G01J 2003/1234* (2013.01); *G01J 2003/1239* (2013.01); *G01J 2003/1291* (2013.01); *G01J 2003/2806* (2013.01); *G01J 2003/2813* (2013.01)

(56) References Cited

U.S. PATENT DOCUMENTS

| | | | |
|---|---|---|---|
| 5,011,279 A | | 4/1991 | Auweter et al. |
| 5,166,755 A | | 11/1992 | Gat |
| 5,218,473 A | | 6/1993 | Seddon et al. |
| 5,272,518 A | | 12/1993 | Vincent |
| 5,784,158 A | | 7/1998 | Stanco et al. |
| 5,872,655 A | | 2/1999 | Seddon et al. |
| 5,949,082 A | | 9/1999 | Schubert et al. |
| 6,057,925 A | | 5/2000 | Anthon |
| 6,075,611 A | | 6/2000 | Dussan |
| 6,700,690 B1 * | | 3/2004 | Buchsbaum ............ G02B 5/20 359/230 |
| 6,836,325 B2 | | 12/2004 | Maczura |
| 6,844,930 B2 | | 1/2005 | Kobayashi et al. |
| 6,909,548 B2 | | 6/2005 | Duggan |
| 7,420,663 B2 | | 9/2008 | Wang et al. |
| 7,460,247 B1 | | 12/2008 | Ackerman |
| 7,907,282 B2 | | 3/2011 | Coates |
| 8,159,668 B2 | | 4/2012 | Malinen et al. |
| 8,476,574 B1 | | 7/2013 | Brown |
| 9,304,039 B2 | | 4/2016 | Tack et al. |
| 9,459,143 B2 | | 10/2016 | Gunji |
| 9,625,628 B2 | | 4/2017 | Hruska et al. |
| 2001/0028458 A1 | | 10/2001 | Xiao |
| 2001/0055116 A1 | | 12/2001 | Maczura |
| 2002/0026981 A1 | | 3/2002 | Fukushima |
| 2002/0039186 A1 | | 4/2002 | Rosenberg |
| 2002/0131047 A1 | | 9/2002 | Zarrabian et al. |
| 2004/0004551 A1 | | 1/2004 | Early |
| 2004/0054248 A1 | | 3/2004 | Kimchy |
| 2004/0218175 A1 | | 11/2004 | Barkhoudarian |
| 2005/0036145 A1 * | | 2/2005 | Meada ............... G01J 3/02 356/419 |
| 2005/0117156 A1 | | 6/2005 | Siepmann et al. |
| 2005/0213092 A1 | | 9/2005 | MacKinnon et al. |
| 2005/0243319 A1 | | 11/2005 | Van Andel et al. |
| 2006/0175547 A1 * | | 8/2006 | DiFoggio ............... G01J 3/02 250/269.1 |
| 2006/0228089 A1 | | 10/2006 | Shimokozono et al. |
| 2007/0068242 A1 | | 3/2007 | DiFoggio |
| 2008/0285165 A1 | | 11/2008 | Wu |
| 2010/0110550 A1 | | 5/2010 | Li et al. |
| 2010/0140373 A1 | | 6/2010 | Myhre |
| 2010/0208348 A1 | | 8/2010 | Feke et al. |
| 2012/0020185 A1 | | 1/2012 | Welker |
| 2012/0120403 A1 | | 5/2012 | Funamoto |
| 2012/0327248 A1 | | 12/2012 | Tack et al. |
| 2013/0141791 A1 | | 6/2013 | Moore et al. |
| 2013/0161544 A1 | | 6/2013 | Ohnishi |
| 2013/0265568 A1 | | 10/2013 | Micheels et al. |
| 2014/0320858 A1 | | 10/2014 | Goldring et al. |
| 2015/0153156 A1 | | 6/2015 | Shah |
| 2015/0153224 A1 | | 6/2015 | Shibayama et al. |
| 2015/0219484 A1 | | 8/2015 | Hruska et al. |
| 2015/0291993 A1 | | 10/2015 | Vela |

FOREIGN PATENT DOCUMENTS

| | | |
|---|---|---|
| CN | 103185637 | 7/2013 |
| CN | 103278861 | 9/2013 |
| EP | 0 295 546 A2 | 12/1988 |
| EP | 0 491 131 A1 | 10/1991 |
| EP | 2600126 A2 | 6/2013 |
| JP | S5760231 A | 4/1982 |
| JP | S5922189 A | 2/1984 |
| JP | H04276526 A | 1/1992 |
| JP | H05322653 A | 12/1993 |
| JP | 2963752 | 10/1999 |
| JP | 2003510560 A | 3/2003 |
| JP | 2005043092 A | 2/2005 |
| JP | 2005517175 A | 6/2005 |
| JP | 2005526332 A | 9/2005 |
| JP | 2009520205 A2 | 5/2009 |
| JP | 2009271046 A | 11/2009 |
| JP | 2011253078 A | 12/2011 |
| JP | 2012013715 A | 1/2012 |
| JP | 2012103208 A | 5/2012 |
| JP | 2013-512445 | 4/2013 |
| JP | 2963752 | 10/2013 |
| JP | 2013242179 A | 12/2013 |
| KR | 10-2004-0110071 | 12/2004 |
| WO | WO 01006232 A2 | 1/2001 |
| WO | WO 02/084238 A2 | 10/2002 |
| WO | WO03100153 A1 | 12/2003 |
| WO | WO 2007078505 A2 | 7/2007 |
| WO | WO 2009/141622 A1 | 11/2009 |
| WO | 2011064403 | 6/2011 |
| WO | WO2012/176851 A | 12/2012 |
| WO | 2013064510 | 5/2013 |
| WO | 2014089120 | 6/2014 |
| WO | 2015015493 | 2/2015 |
| WO | WO 2015050464 A | 4/2015 |

OTHER PUBLICATIONS

Extended European Search Report corresponding to EP 16 18 2550, dated Apr. 13, 2017, 15 pages.
"CLARIOstar® High Performance Microplate reader with Advanced LVF Monochromators™", BMG Labtech The Microplate Reader Company, Aug. 2013, 8 pages.
U.S. Appl. No. 14/818,179, entitled "In-Situ Spectral Process Monitoring", by Catching et al., filed Aug. 5, 2015, 32 pages.
Partial European Search Report corresponding to EP 16182511.2, dated Jan. 3, 2017, 7 pages.
Xin et al., "A vector water jet propulsion method for autonomous underwater vehicles", Ocean Engineering, vol. 74, Nov. 2013, 8 pages, XP028778880.
Extended European Search Report corresponding to EP 16 18 2511, dated Apr. 3, 2017, 13 pages.
Extended European Search Report corresponding to EP 15 74 3537, dated Aug. 7, 2017, 9 pages.
PCT/US2015/013415 Search Report dated Mar. 30, 2015.

* cited by examiner

OPTICAL FILTER AND SPECTROMETER

BACKGROUND

An optical filter may be used to transmit a spectral band or a spectral component of incoming light. A high pass filter, for example, transmits light at wavelengths longer than an edge wavelength of the filter. Conversely, a low pass filter transmits light at wavelengths shorter than an edge wavelength. A bandpass filter transmits light at wavelengths proximate to a center wavelength of the filter within a bandwidth of the filter. A tunable bandpass filter is an optical filter, the center wavelength of which may be adjusted or tuned.

A spectrometer may measure an optical spectrum of incoming light. A scanning-type spectrometer may use one or more tunable bandpass filters to select different spectral components of the incoming light. A scanning-type spectrometer operates by scanning the center wavelength of the tunable bandpass filter while measuring optical power levels of light transmitted through the tunable bandpass filter, so as to obtain the optical spectrum. Alternatively, a polychromator-type spectrometer uses a wavelength-dispersing element optically coupled to a photodetector array for parallel detection of the optical spectrum.

Conventional optical filters and spectrometers are bulky, which limits their usefulness in portable light-sensing devices and applications. Linearly variable filters have been used in spectrometers to provide a wavelength separating function. Referring to FIG. 1A, a conventional linearly variable filter 10 may be illuminated with white light, which includes top 11, middle 12, and bottom 13 multi-wavelength light beams. The top 11, middle 12, and bottom 13 multi-wavelength light beams may strike the linearly variable filter 10 at respective top 11A, middle 12A, and bottom 13A locations. The linearly variable filter 10 may have a center wavelength of a passband varying linearly along an x-axis 18. For instance, the filter 10 may transmit a short wavelength peak 11B at the top location 11A; a middle wavelength peak 12B at the middle location 12A; and a long wavelength peak 13B at the bottom location 13A.

Referring to FIG. 1B, a conventional spectrometer 19 may include the linearly variable filter 10 of FIG. 1A, a tapered light pipe 14 disposed upstream of the linearly variable filter 10, and a linear array 15 of photodetectors disposed downstream of the linearly variable filter 10. In operation, non-collimated incoming light 16 may be conditioned by the light pipe 14 to produce a partially collimated light beam 17. The linearly variable filter 10 may transmit light at different wavelengths as explained above with reference to FIG. 1A. The tapered light pipe 14 may reduce a solid angle of the incoming light 16, thereby improving spectral selectivity of the linearly variable filter 10. The linear array 15 of photodetectors may detect optical power levels of light at different wavelengths, thereby obtaining an optical spectrum, not shown, of the incoming light 16.

The tapered light pipe 14 may often be the largest element of the spectrometer 19. A collimating element, such as tapered light pipe 14, may be needed because without it, the spectral selectivity of the linearly variable filter is degraded. This may happen because the linearly variable filter 10 includes a stack of thin dielectric films. The wavelength-selective properties of thin film filters are generally dependent on the angle of incidence of incoming light, which may deteriorate spectral selectivity and wavelength accuracy of thin film filters.

DETAILED DESCRIPTION

The following detailed description refers to the accompanying drawings. The same reference numbers in different drawings may identify the same or similar elements.

Figure 1A:
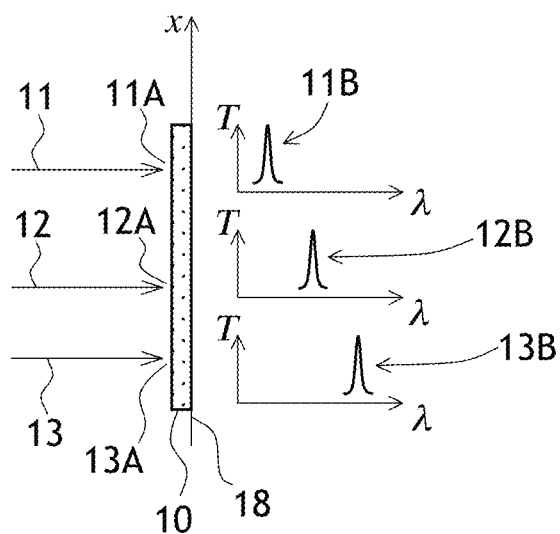
FIG. 1A is a diagram of a conventional linearly variable filter.
Figure 1B:
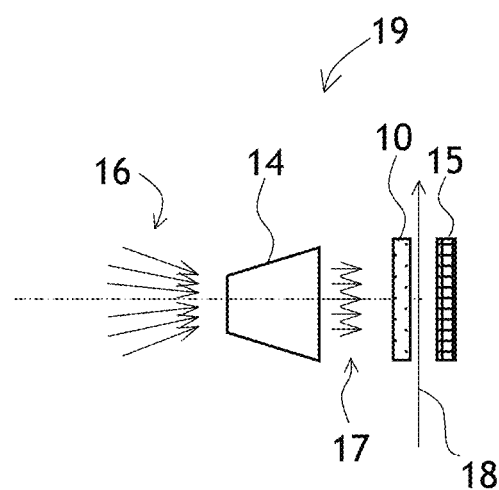
FIG. 1B is a diagram of a conventional optical spectrometer that includes the linearly variable filter of FIG. 1A.
Figure 2A:
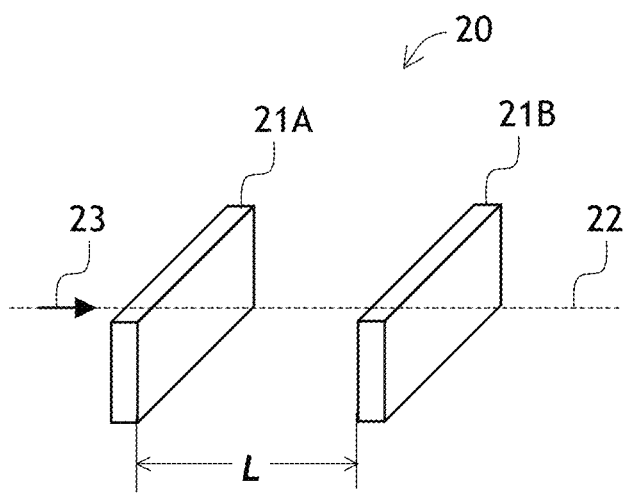
FIG. 2A is a diagram of an optical filter, including a pair of laterally variable bandpass filters spaced apart and fixed relative to each other.
Figure 2B:
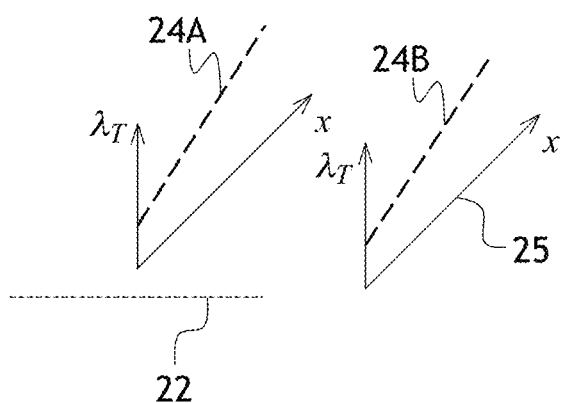
FIG. 2B is a diagram of center wavelength dependences of the laterally variable bandpass filters of FIG. 2A.

FIGS. 2A and 2B are diagrams of an optical assembly 20 (FIG. 2A) for spectral filtering of light according to an example implementation described below. For example, the optical assembly 20 may include sequentially disposed first 21A and second 21B laterally variable bandpass optical filters separated by a distance L in an optical path 22 of signal light 23. The second laterally variable bandpass optical filter 21B may be fixed relative to the first laterally variable bandpass optical filter 21A in the optical path 22 downstream of the first laterally variable bandpass optical filter 21A. In other words, the second laterally variable bandpass optical filter 21B may be disposed and fixed so that it may not be moved laterally with respect to the first laterally variable bandpass optical filter 21A. As shown in FIG. 2B, the first 21A and second 21B laterally variable bandpass optical filters each may have a bandpass center wavelength $\lambda_T$ varying in a mutually coordinated fashion, that is, varying with distance along a common first direction 25 represented by x-axis. The first direction 25 is transversal to the optical path 22. The term "laterally variable" as used herein is defined to mean that the bandpass center wavelength $\lambda_T$ varies in any direction transversal to the optical path 22 such as, for example, the first direction 25. By way of a non-limiting example, the bandpass center wavelength $\lambda_T$ of both the first 21A and second 21B laterally variable bandpass optical filters of FIG. 2A may have respective monotonic, e.g. linear dependences 24A, 24B, as shown in FIG. 2B. The center wavelength dependences $\lambda_{1T}(x)$ and $\lambda_{2T}(x)$ of the first 21A and second 21B laterally variable bandpass optical filters, respectively, on the distance along the first direction 25, represented by the x-coordinate, may be identical, or may be shifted with respect to each other. For example, the center wavelength dependences $\lambda_{1T}(x)$ and $\lambda_{2T}(x)$ may be such that $\lambda_{2T}(x)=\lambda_{1T}(x+x_0)$, where $x_0$ is a constant; or scaled e.g. $\lambda_{2T}(x)=c\lambda_{1T}(x)$, where c is a constant e.g. $0.9<c<1.1$. The term "coordinated fashion" or "mutually coordinated" as used herein with respect to the bandpass center wavelength $\lambda_T$ is defined to mean a pre-determined functional relationship between the center wavelength dependences $\lambda_{1T}(x)$ and $\lambda_{2T}(x)$ of the first 21A and second 21B laterally variable bandpass optical filters, respectively.

The configuration of the optical assembly 20 may enable a dependence of spectral selectivity of the optical assembly 20 on a degree of collimation of the signal light 23 to be lessened as compared to a corresponding dependence of spectral selectivity of the second laterally variable bandpass optical filter 21B on the degree of collimation of the signal light 23. This performance improvement of the optical assembly 20 may result from a spatial filtering effect illustrated in FIG. 2C. In monochromatic light at a wavelength $\lambda_0$, the first 21A and second 21B laterally variable bandpass optical filters may be approximately represented by slits having "openings" 26 corresponding to locations along the x-axes where the center wavelength $\lambda_T=\lambda_0$. Outside of the "openings" 26, the first 21A and second 21B laterally variable bandpass optical filters may be essentially opaque for the monochromatic light at the wavelength $\lambda_0$. The "openings" 26 define an acceptance cone, or solid angle 27 (2θ), which depends on the inter-filter distance L. Any rays outside of the solid angle 27 may be blocked, thus improving the spectral selectivity of the second laterally variable bandpass optical filter 21B.

Figure 2C:
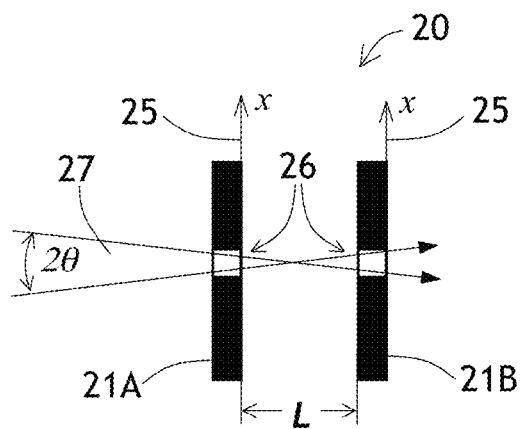
FIG. 2C is a diagram of a side view of the optical filter of FIG. 2A illustrating a principle of spatial filtering by the optical filter.
Figure 3:
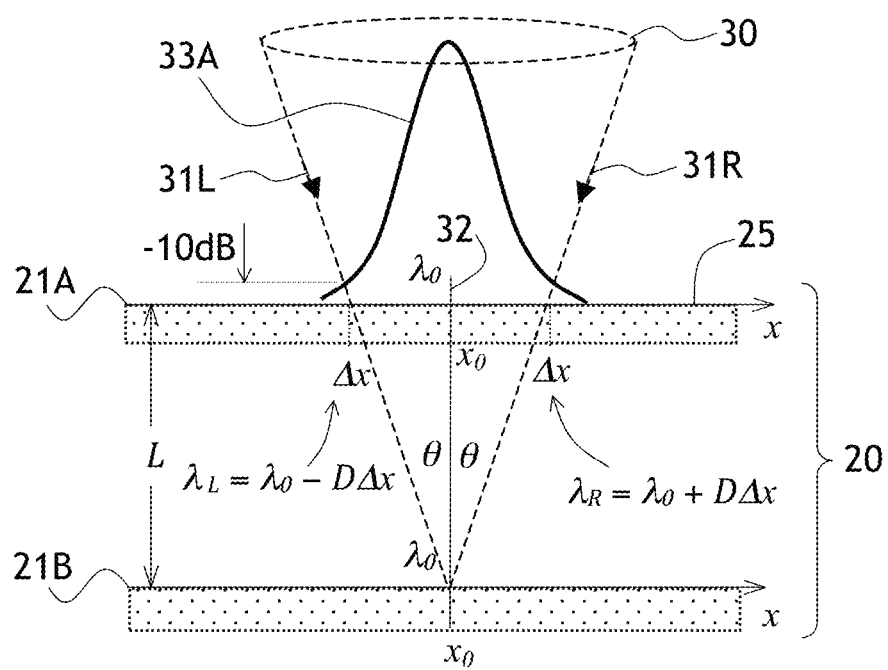
FIG. 3 is a diagram of the optical filter of FIG. 2A in a side cross-sectional view showing an acceptance angle of the optical filter.

The operation of the optical assembly 20 of FIGS. 2A-2C may be further explained by referring to FIG. 3 showing the optical assembly 20 in a side cross-sectional view. As shown in FIG. 3, the center wavelength $\lambda_T$ may increase from left to right along the first direction 25, shown as the x-coordinate, for both the first 21A and second 21B laterally variable bandpass optical filters. In FIG. 3, the bandpass center wavelengths $\lambda_T$ of the first 21A and second 21B laterally variable bandpass optical filters may be linearly dependent on the x-coordinate:

$$\lambda_T = \lambda_0 + D\Delta x \quad (1)$$

where $\lambda_0$ represents a reference bandpass center wavelength at a reference point $x_0$, D represents the proportionality coefficient, herein termed a "slope" of a laterally variable filter, and $\Delta x$ represents an offset from the reference point $x_0$. The slope D may correspond to the slopes of the linear dependences 24A and 24B in FIG. 2B, which may, but does not have to, be identical to each other. Deviations from identical slopes of the linear dependences 24A and 24B may be advantageous in some applications.

In the example implementation of FIG. 3, the first 21A and second 21B laterally variable bandpass optical filters may be aligned with each other, so that the reference point $x_0$ corresponding to the reference bandpass center wavelength $\lambda_0$ of the second laterally variable bandpass optical filter 21B is disposed directly under the reference point $x_0$ corresponding to the reference bandpass center wavelength $\lambda_0$ of the first laterally variable bandpass optical filter 21A. The first laterally variable bandpass optical filter 21A may function as a spatial filter for the second laterally variable bandpass optical filter 21B, defining an angle of acceptance 30 for the second laterally variable bandpass optical filter 21B. The angle of acceptance 30 may be limited by left 31L and right 31R marginal rays at the reference wavelength $\lambda_0$, each propagating at the angle θ to a normal 32 to the first 21A and second 21B laterally variable bandpass optical filters and striking second laterally variable bandpass optical filter 21B at the same reference point $x_0$. The angle of acceptance 30 may be derived from a passband 33A of the first laterally variable bandpass optical filter 21A as follows.

In the geometry illustrated in the example implementation of FIG. 3, the left marginal ray 31L may strike the first laterally variable bandpass optical filter 21A at a location $x_0-\Delta x$. Transmission wavelength $\lambda_L$ at that location may be, according to Eq. (1), $\lambda_L=\lambda_0-D\Delta x$. Since the left marginal ray 31L is at the reference wavelength $\lambda_0$, the left marginal ray 31L may be attenuated depending on the width of the passband 33A of the first laterally variable bandpass optical filter 21A; for sake of this example, a 10 dB bandwidth is taken to be $2D\Delta x$. Thus, the left marginal ray 31L may be attenuated by 10 dB. Similarly, the right marginal ray 31R may strike the first laterally variable bandpass optical filter 21A at a location $x_0+\Delta x$. Transmission wavelength $\lambda_R$ at that location may be, according to Eq. (1), $\lambda_R=\lambda_0+D\Delta V$. The right marginal ray 31R may also be attenuated by 10 dB. All rays at the reference wavelength $\lambda_0$ within the acceptance angle 30 may be attenuated by a value smaller than 10 dB; and all rays at the reference wavelength $\lambda_0$ outside the acceptance angle 30 may be attenuated by a value larger than 10 dB. The first laterally variable bandpass optical filter 21A may function as a spatial filter, effectively limiting the numerical aperture (NA) of incoming light to be separated in individual wavelengths by the second laterally variable bandpass optical filter 21B. This may result in reduction of the dependence of spectral selectivity of the optical assembly 20 in comparison with the corresponding dependence of the spectral selectivity of the single second laterally variable bandpass optical filter 21B on the degree of collimation of the signal light 23. If the first laterally variable bandpass optical filter 21A were absent in the optical assembly 20, the spectral selectivity of the optical assembly 20 would be much more dependent on the degree of collimation of the signal light 23. Typically, the signal light 23 may result from scattering or luminescence of a sample, not shown, so that the signal light 23 is not collimated. The lack of collimation of the signal light 23 in the absence of the first laterally variable bandpass optical filter 21A would result in worsening of overall spectral selectivity unless a dedicated collimating element, such as a tapered light pipe, is used. Herein, the term "spectral selectivity" includes such parameters as passband width, stray light rejection, in-band and out-of-band blocking, etc.

For small angles θ, for example θ<5°

$$\theta \approx \Delta x/L \quad (2), \text{ or}$$

$$L \approx \Delta x/\theta \quad (3)$$

When the space between the first 21A and second 21B laterally variable bandpass optical filters is filled with a transparent medium having a refractive index n, Eq. (3) becomes $$L/n \approx \Delta x/\theta \quad (4)$$

Eq. (4) may define an approximate relationship between the inter-filter distance L, the refractive index n of the inter-filter gap, a lateral distance $\Delta x$ along the first direction 25, corresponding to a bandwidth of the first laterally variable bandpass optical filter 21A, and the resulting acceptance half-angle θ. A more precise relationship may take into account the wavelength offset due to non-zero angle of incidence, which typically results in a blue shift (i.e. towards shorter wavelength) of the bandpass center wavelength $\lambda_T$. For instance, the right marginal ray 31R at the reference wavelength $\lambda_0$ striking the first laterally varying bandpass optical filter 21A at the position $x_0 + \Delta x$ may be tilted by the angle θ, which shifts the transmission characteristic of the first laterally varying bandpass optical filter 21A to shorter wavelengths. If this wavelength dependence is to be accounted for, the shoulders of the passband 33A may shift to the left i.e. shorter wavelengths:

$$\lambda_1 \approx [(\lambda_0 + D\Delta x)(n_{eff}^2 - \theta^2)^{1/2}]/n_{eff} \quad (5)$$

where $n_{eff}$ represents an effective refractive index of the first laterally variable bandpass optical filter 21A.

Although in FIG. 2B, the first 21A and second 21B laterally variable bandpass filters have linearly variable bandpass center wavelengths $\lambda_T$ as defined by Eq. (1) above, the center wavelengths $\lambda_T$ of the first 21A and second 21B laterally variable bandpass optical filters may be monotonically non-linearly, for example parabolically or exponentially, increasing or decreasing in the first direction 25. The bandpass center wavelengths $\lambda_T$ dependence may also be non-gradual, e.g., stepwise. The dependence of the bandpass center wavelength $\lambda_T$ on the x-coordinate along the first direction 25 of the first 21A and second 21B laterally variable filters may be identical, or may be different to enable optimizing or varying of the acceptance angle and/or wavelength response of the optical assembly 20. In one embodiment, the bandpass center wavelengths $\lambda_T$ of the first 21A and second 21B laterally variable bandpass optical filters may be aligned with each other, such that a line connecting positions corresponding to a same bandpass center wavelength $\lambda_T$ of the first 21A and second 21B laterally variable bandpass optical filters forms an angle of less than 45 degrees with the normal 32 to the second laterally variable bandpass optical filter 21B. For non-zero angles with the normal 32, the acceptance cone 30 may appear tilted. Thus, it may be possible to vary the acceptance cone 30 direction by offsetting the first 21A and second 21B laterally variable bandpass optical filters relative to each other in the first direction 25. Furthermore, the angle may vary along the first direction (x-axis) 25.

For a better overall throughput, it may be preferable to have a lateral distance $\Delta x_1$ along the first direction 25, corresponding to a bandwidth of the first laterally variable bandpass optical filter 21A larger than a corresponding lateral distance $\Delta x_2$ along the first direction 25, corresponding to a bandwidth of the second laterally variable bandpass optical filter 21B. In one embodiment, the first 21A and second 21B laterally variable bandpass optical filters each may have a 3 dB passband no greater than 10% of a corresponding bandpass center wavelength $\lambda_T$.

The first 21A and/or second 21B laterally variable bandpass optical filters may include a thin film layer stack including two, three, and more different materials, e.g., high-index and/or absorbing layers may be used to reduce overall thickness of each of the first 21A and second 21B laterally variable bandpass optical filters. The first 21A and/or the second 21B laterally variable bandpass optical filters may include diffraction gratings e.g. sub-wavelength gratings, dichroic polymers, etc. An additional laterally variable bandpass optical filter may be provided in the optical path, the additional filter having a bandpass center wavelength varying in a coordinated fashion with the bandpass center wavelengths of the first 21A and second 21B laterally variable bandpass optical filters.

Figure 4A:
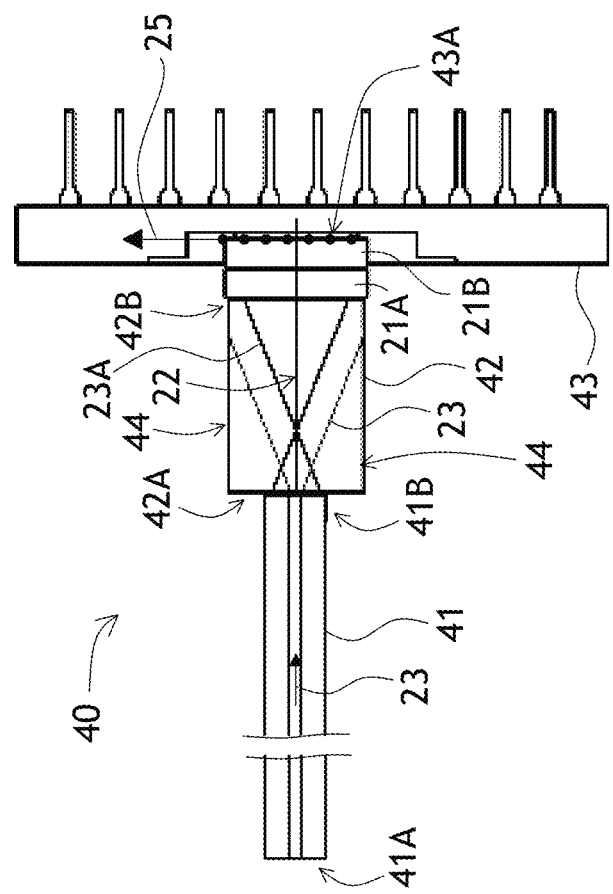
FIG. 4A is a diagram of a top view of a fiber-coupled optical spectrometer assembly including a straight optical conduit.
Figure 4B:
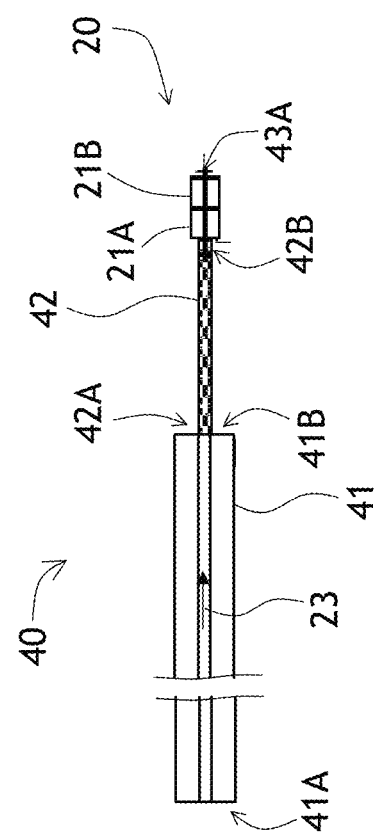
FIG. 4B is a diagram of a side cross-sectional view of the fiber-coupled optical spectrometer assembly of FIG. 4A.

FIGS. 4A and 4B are diagrams of an optical spectrometer assemblies 40 according to an example implementation described below. The optical spectrometer assembly 40 of FIGS. 4A and 4B may include, for example, the optical assembly 20 of FIG. 2A and may further include an optical fiber 41 extending between its first 41A and second 41B ends for conducting the signal light 23 from the first end 41A to the second end 41B.

An optical conduit 42 may extend between its first 42A and second 42B surfaces. The first surface 42A may be optically coupled, i.e. via an air gap or by a direct physical contact, to the second end 41B of the optical fiber 41 for receiving the signal light 23 and conducting the signal light 23 in the optical conduit 42 from the first surface 42A to the second surface 42B. The second surface 42B may be optically coupled to the first laterally variable bandpass optical filter 21A for receiving the signal light 23 for propagation along the optical path 22. A multi-element sensor 43, such as a photodetector array, may be optically coupled to the second laterally variable bandpass optical filter 21B. The sensor 43 may include photodetectors 43A disposed along the first direction 25 for wavelength selective detection of the signal light 23 propagated through the second laterally variable bandpass optical filter 21B.

In the exemplary embodiment shown in FIGS. 4A and 4B, the optical conduit 42 may include a planar parallel slab of homogeneous transparent material, for example glass or an injection-molded transparent plastic material. The slab may have a plurality of external surfaces, for example the first 42A and second 42B surfaces, which may be flat or curved. The slab may be configured for unconstrained propagation of the signal light 23, e.g. the slab may be continuous or hollow. The slab may be disposed generally parallel to the first direction 25, and optionally mechanically coupled to the first laterally variable bandpass optical filter 21A.

A portion 23A of the signal light 23 may be reflected from the first laterally variable bandpass optical filter 21A. The portion 23A may include light at wavelengths other than the transmission wavelength at a particular reflection location of the first laterally variable bandpass optical filter 21A. To recycle the portion 23A, the optical conduit 42 may include a reflective wall or walls 44 for redirecting at least a portion of the reflected light portion 23A back to the first laterally variable bandpass optical filter 21A.

Figure 4C:
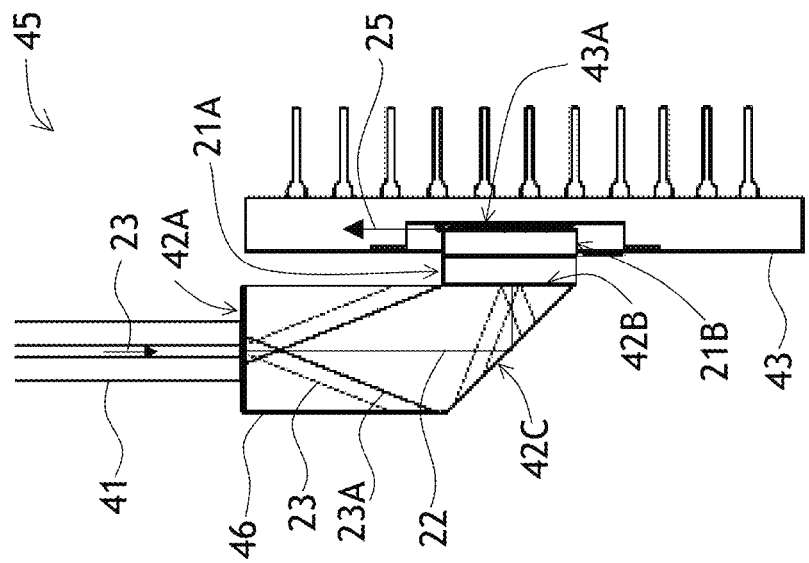
FIG. 4C is a diagram of a top view of a variant of the fiber-coupled optical spectrometer assembly of FIG. 4A.

Turning to FIG. 4C, an optical spectrometer assembly 45 is shown according to an example implementation described below. The optical spectrometer assembly 45 of FIG. 4C may further include an elbowed optical conduit 46 instead of the straight optical conduit 42. The elbowed optical conduit 46 may enable a more compact mechanical configuration. The elbowed optical conduit 46 may have the first surface 42A, the second surface 42B, and a third surface 42C, e.g. a flat or curved surface disposed in the optical path 22 between the first 42A and second 42B surfaces, for receiving the signal light 23 from the first surface 42A and reflecting the signal light 23 towards the second surface 42B. The third surface 42C may be optionally mirrored, or left uncoated when the refractive index of the elbowed optical conduit 46 is high enough for the signal light 23 to reflect by total internal reflection (TIR): $n>1/\sin(\alpha)$, where n is the refractive index of the conduit 46, and $\alpha$ is the angle of incidence of the signal light 23 on the third surface 42C. The straight optical conduit 42 or the elbowed optical conduit 46 may include multiple conduit branches coupled to multiple individual optical fibers, not shown.

Figure 5:
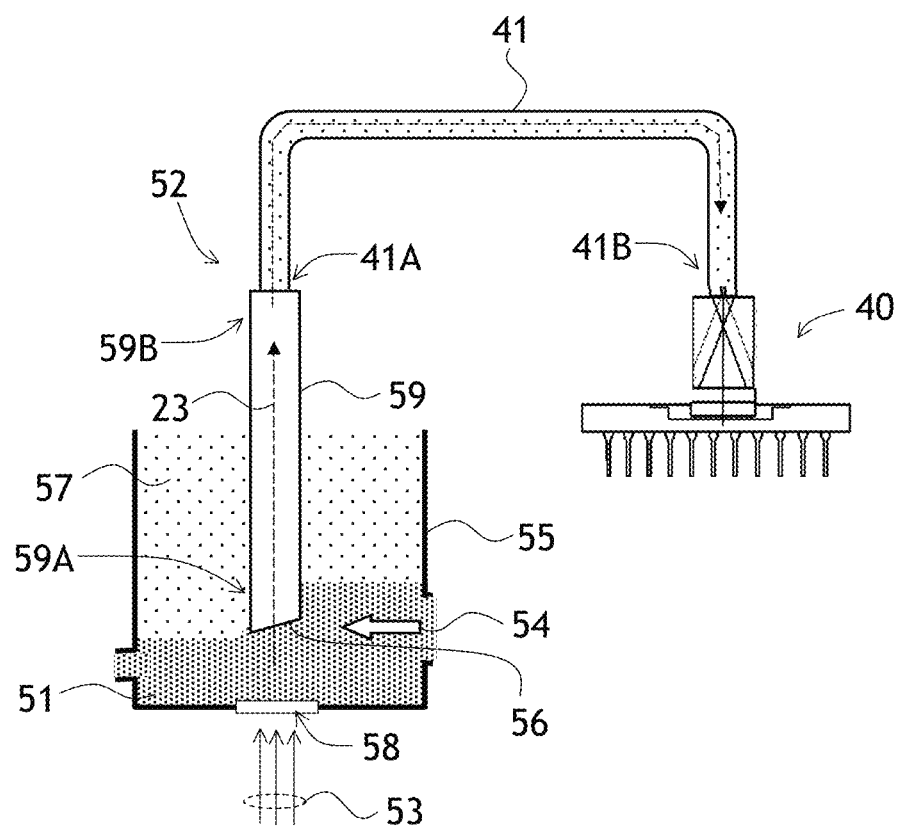
FIG. 5 is a diagram of a side view of the optical spectrometer assembly of FIGS. 4A and 4B including a slanted relay lightpipe for transmission spectral measurements of fluids or flowing granular materials.

Referring to FIG. 5, an optical spectrometer assembly 50 is shown according to an example implementation described below. The optical spectrometer assembly 50 of FIG. 5 may include an optical probe 52 optically coupled to the first end 41A of the optical fiber 41, for collecting the signal light 23 emanating from a fluid or granular sample 51 when the sample 51 is illuminated with illuminating light 53, and for coupling the signal light 23 to the first end 41A of the optical fiber 41. In the example implementation shown in FIG. 5, the fluid or granular sample 51 is held in a cuvette 55 having a transparent window 58 at the bottom for transmitting through the illuminating light 53. For instance, the signal light 23 may represent transmitted illuminating light 53, or scattered illuminating light 53, or luminescence, such as fluorescence or phosphorescence.

Still referring to FIG. 5, the optical probe 52 may include a relay lightpipe 59 extending between its first 59A and second 59B ends. The first end 59A, herein termed "distal" end, that is the farthest from the optical fiber 41, may be configured for contacting or inserting into the sample 51, thereby collecting the signal light 23 emanating from the sample 51, and the second end 59B, herein termed "proximal" end, that is, the closest to the optical fiber 41, may be configured for optical and mechanical coupling to the first end 41A of the optical fiber 41. The relay lightpipe 59 of the optical probe 52 may be configured for unconstrained propagation of the signal light 23 in bulk of the relay lightpipe from the first 59A to the second 59B end. For instance, the relay lightpipe 59 may be made of glass or a rigid transparent, chemically inert plastic, so that it can be inserted through a fluid or granular overlayer 57 down to the sample 51. The relay lightpipe 59 may also be made hollow, with mirrored internal walls.

In the example implementation shown in FIG. 5, the first (distal) end 59A of the relay lightpipe 59 may include a slanted optical surface 56, which may cause the sample 51 flowing in a direction 54 to exert a pressure onto the slanted optical surface 56, which may facilitate the collection of the signal light 23, especially for granular samples 51 or samples 51 including a fluid suspension of a solid material.

It is to be understood that the relay lightpipe 59 is only one possible embodiment of the optical probe 52. Other embodiments of the optical probe 52 may include an irradiance probe, a reflection/backscatter probe, a transmission cuvette, an oxygen probe, a fluorescence or phosphorescence probe, etc. The optical fiber 41 may include a bifurcated fiber including a branch for delivering the illuminating light 53 to the transmission cuvette, for example.

Figure 6A:
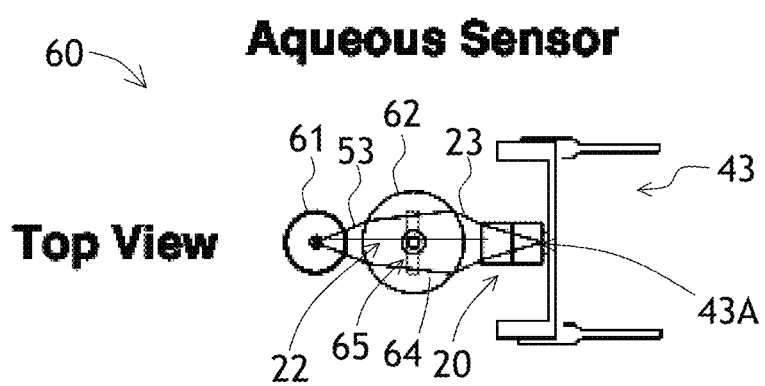
FIGS. 6A and 6B are diagrams of top and side cross-sectional views, respectively, of a spectrometer assembly equipped with a flow cuvette having a slab cavity.
Figure 6B:
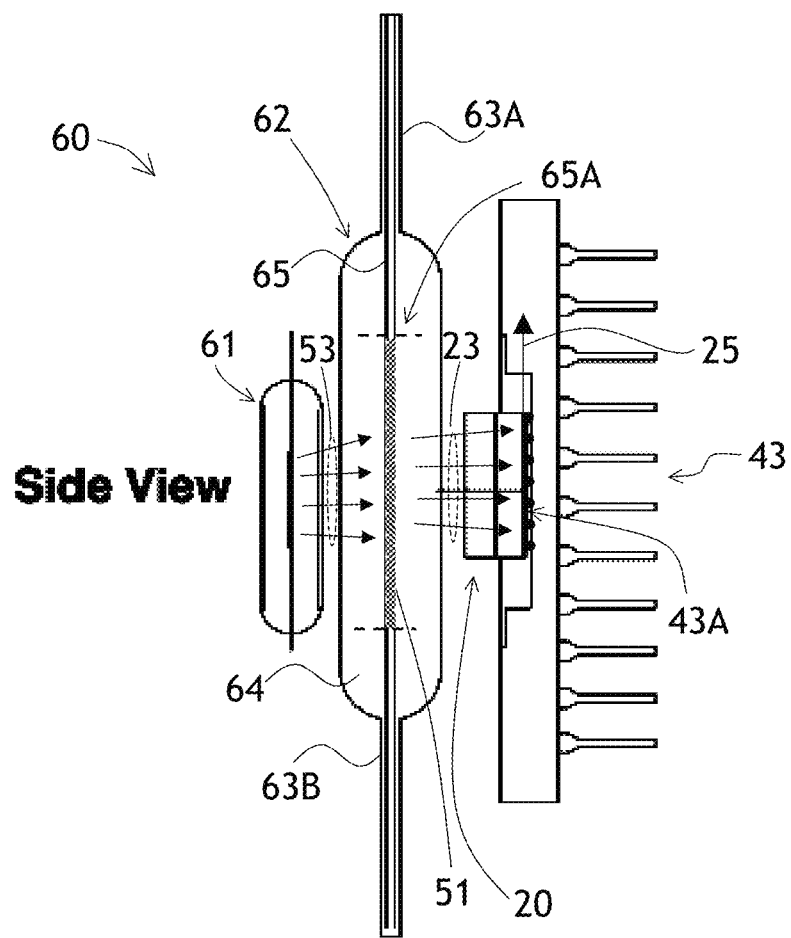

Referring now to FIGS. 6A and 6B, an example implementation of a flow spectrometer optical assembly 60 may include a light source 61 for providing the illuminating light 53, an elongated optical cuvette 62 extending generally parallel to the first direction 25 (FIG. 6B), the optical assembly 20 of FIG. 2A, and the sensor 43.

The elongated optical cuvette 62 may include an inlet 63A for receiving the sample 51 in fluid form, a substantially transparent sidewall 64 defining a cavity 65 in fluid communication with the inlet 63A, for receiving and containing the sample 51 while transmitting the illuminating light 53 through the sidewall 64 for illuminating the sample 51 received in the cavity 65. Upon illumination, the sample 51 received by the cavity 65 emits the signal light 23. The transparent sidewall 64 may be configured for transmitting the signal light 23 through the transparent sidewall 64 for optical coupling the signal light 23 to the first laterally variable bandpass optical filter 21A for propagation along the optical path 22. The elongated optical cuvette 62 may further include an outlet 63B in fluid communication with the cavity 65, for outputting the sample 51 illuminated with the illuminated light 53.

The sensor 43 may be optically coupled to the second laterally variable bandpass optical filter 21B. The photodetectors 43A of the sensor 43 may be disposed along the first direction 25 for wavelength selective detection of the signal light 23 propagated through the second laterally variable bandpass optical filter 21B. For a more uniform illumination of the sample 23 in the cavity 65, the light source 61 may be elongated as shown in FIG. 6B, extending generally parallel to the first direction 25. For example, an incandescent lamp having a tungsten spiral extending along the first direction 25 may be used. The wall 64 of the elongated optical cuvette 62 may function as a lens facilitating refracting or focusing the illuminating light 53 onto the cavity 65 containing the sample 51, and/or facilitating refracting or focusing the signal light 23 onto the sensor 43 (FIG. 6A).

In the example implementation shown in FIGS. 6A and 6B, the cavity 65 has a slab portion 65A extending parallel to the first direction 25, e.g. a planar parallel slab. This may enable the liquid sample 23 to be thin in the cavity 65, for example thinner than 1 mm, or thinner than 2 mm if the light source 61 has a high optical power, for instance when the light source 61 includes, or is coupled to, a laser source. Small thickness may be useful for obtaining absorption spectra of aqueous solutions dominated by vibrational frequencies of water.

Figure 7A:
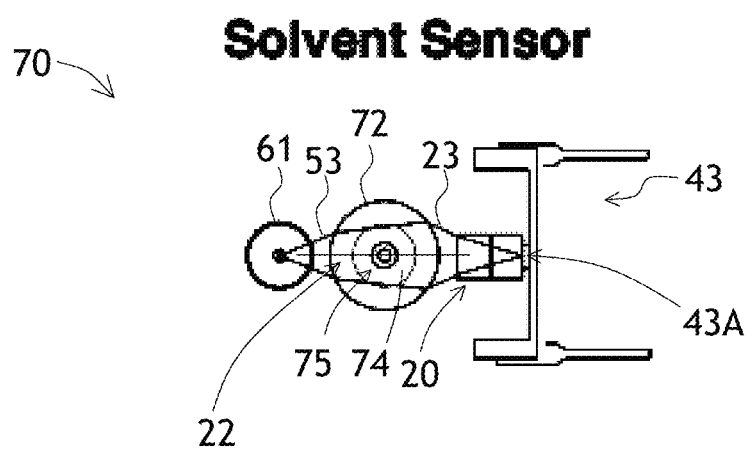
FIGS. 7A and 7B are diagrams of top and side cross-sectional views, respectively, of a spectrometer assembly equipped with a flow cuvette having a cylindrical cavity.
Figure 7B:
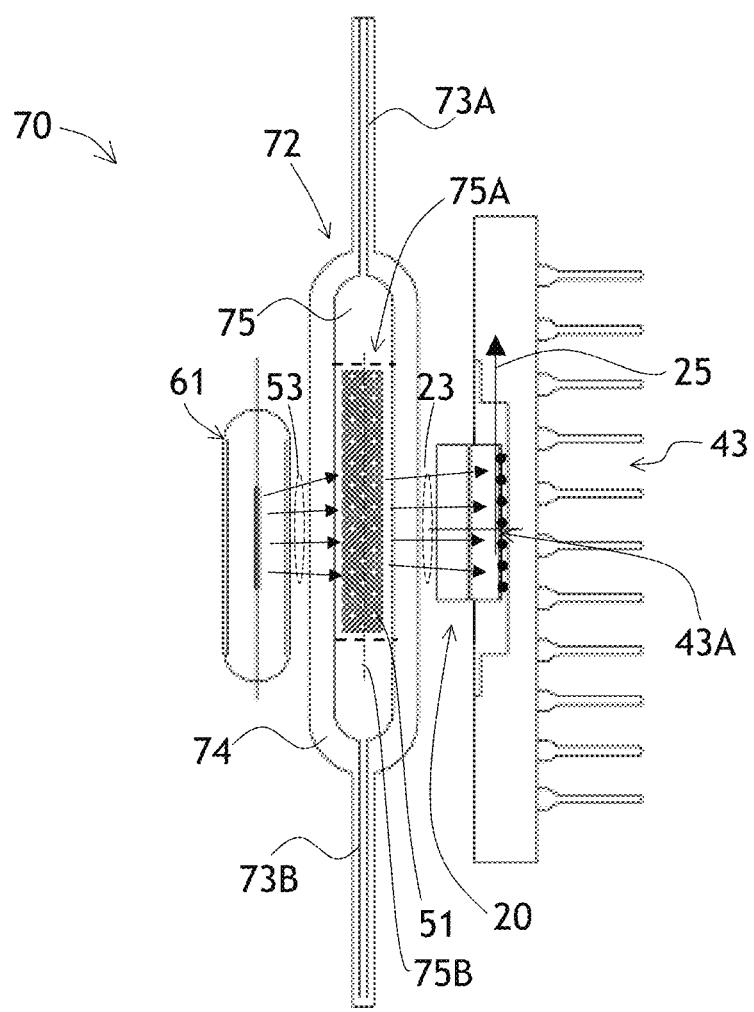

Turning to FIGS. 7A and 7B, an example implementation of a flow spectrometer optical assembly 70 is shown. The flow spectrometer optical assembly 70 of FIGS. 7A and 7B includes a flow cuvette 72 having an inlet 73A, an outlet 73B, a transparent sidewall 74 defining a cavity 75 having a cylindrical portion 75A having an optical axis 75B, which may extend substantially parallel to the first direction 25. The cylindrical portion 75A of the cavity 75 allows for a larger volume of the sample 51 to be held therein, which may be more suitable for obtaining absorption spectra of organic solutions. Specific applications may require other path lengths. Similarly to the flow spectrometer optical assembly 60 of FIGS. 6A and 6B, the transparent sidewall 74 of the flow spectrometer optical assembly 70 of FIGS. 7A and 7B may function as a lens facilitating refracting the illuminating light 53 onto the cavity 75 containing the sample 51 and/or facilitating focusing the signal light 23 onto the sensor 43 (FIG. 7A).

In one embodiment, the sensor 43 may include a 2D array of photodetectors, including multiple rows of the photodetectors 43A. Preferably, each such row may extend parallel to the first direction 25. The 2D array of photodetectors may be used to simultaneously obtain spectra of the signal light 23 in different wavelength ranges.

Figure 8A:
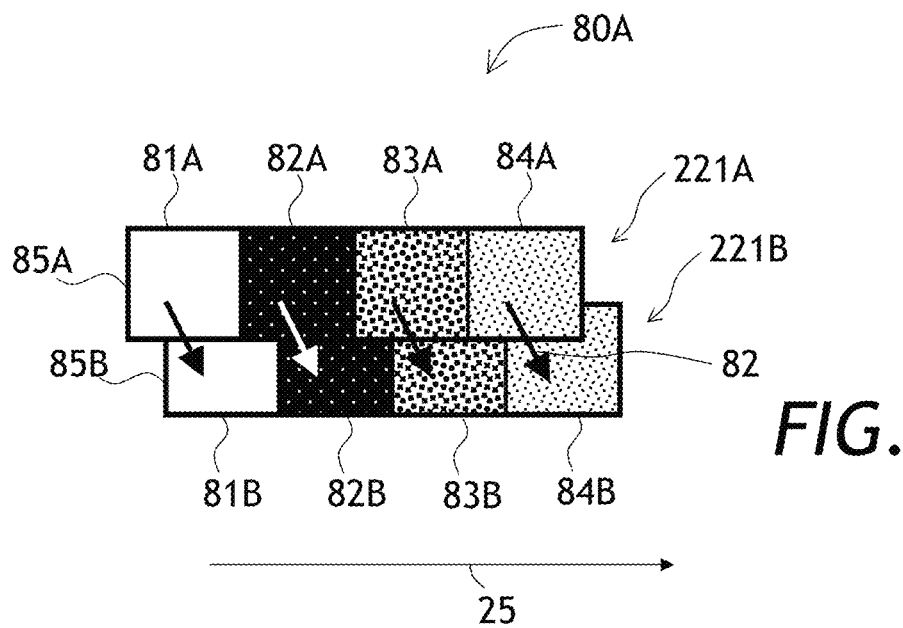
FIGS. 8A-8D are schematic plan views of segmented laterally variable optical filters.

In an example implementation, the first 21A or second 21B laterally variable bandpass optical filters, or both 21A and 21B laterally variable bandpass optical filters of the optical assembly 20 (FIG. 2A) may be segmented. FIGS. 8A-8D are diagrams of schematic plan views of optical assemblies according to example implementations described below. Referring specifically to FIG. 8A, first 221A and second 221B segmented laterally variable bandpass optical filters of an optical assembly 80A may each include an array 85A of bandpass optical filter segments e.g. 81A, 82A, 83A, 84A for the first segmented laterally variable bandpass optical filter 221A, arranged side by side in the first direction 25; and an array 85B of bandpass optical filter segments 81B, 82B, 83B, 84B for the second segmented laterally variable bandpass optical filter 221B, arranged side by side in the first direction 25.

Each bandpass optical filter segment 81A-84A of the first segmented laterally variable bandpass optical filter 221A may have a laterally invariable, i.e. constant, transmission center wavelength $\lambda_T$ different from a transmission center wavelength $\lambda_T$ of an immediate neighboring bandpass optical filter segment 81A-84A. For example, the transmission center wavelength $\lambda_T$ of the second bandpass optical filter segment 82A may be different from the transmission center wavelength $\lambda_T$ of the first bandpass optical filter segment 81A and the third bandpass optical filter segment 83A, and so on. The same rule may hold for the second segmented laterally variable bandpass optical filter 221B: each bandpass optical filter segment 81B, 82B, 8AB, 84B of the second segmented laterally variable bandpass optical filter 221B may have a laterally invariable, i.e. constant, transmission center wavelength $\lambda_T$ different from a transmission center wavelength $\lambda_T$ of an immediate neighboring bandpass optical filter segment 81B-84B. As a result, the bandpass center wavelengths of the first 221A and second 221B segmented laterally variable bandpass optical filters may laterally vary stepwise from segment to segment, and/or non-monotonically from segment to segment.

As illustrated by arrows 82 in FIG. 8A, the transmission center wavelengths $\lambda_T$ of the bandpass optical filter segments 81A, 81B, 81C, and 81D of the first 221A and second 221B segmented laterally variable bandpass optical filters may be mutually coordinated. By way of a non-limiting example, the transmission center wavelengths $\lambda_T$ may be equal to each other: the transmission center wavelength $\lambda_T$ of the first bandpass optical filter segment 81A may be equal to the transmission center wavelength $\lambda_T$ of the first second bandpass optical filter segment 81B, and so on. The transmission bandwidths of the corresponding bandpass optical filter segments of the first 221A and second 221B segmented laterally variable bandpass optical filters may be equal to each other, e.g. no greater than 10%, and more preferably no greater than 2% of the corresponding transmission center wavelengths $\lambda_T$ of the bandpass optical filter segments 81A-84A. For a better overall throughput of the optical assembly 80A, transmission bandwidths of the bandpass optical filter segments 81A-84A of the first segmented laterally variable bandpass optical filter 221A may be greater than transmission bandwidths of the corresponding bandpass optical filter segments 81B-84B of the second segmented laterally variable bandpass optical filter 221B. By way of an illustrative, non-limiting example, the transmission bandwidths of the bandpass optical filter segments 81A-84A of the first segmented laterally variable bandpass optical filter 221A may be no greater than 2% of the corresponding transmission center wavelengths $\lambda_T$ of the bandpass optical filter segments 81A-84A, while the transmission bandwidths of the bandpass optical filter segments 81B-84B of the second segmented laterally variable bandpass optical filter 221B may be no greater than 1% of the corresponding transmission center wavelengths $\lambda_T$ of the bandpass optical filter segments 81B-84B.

Figure 8B:
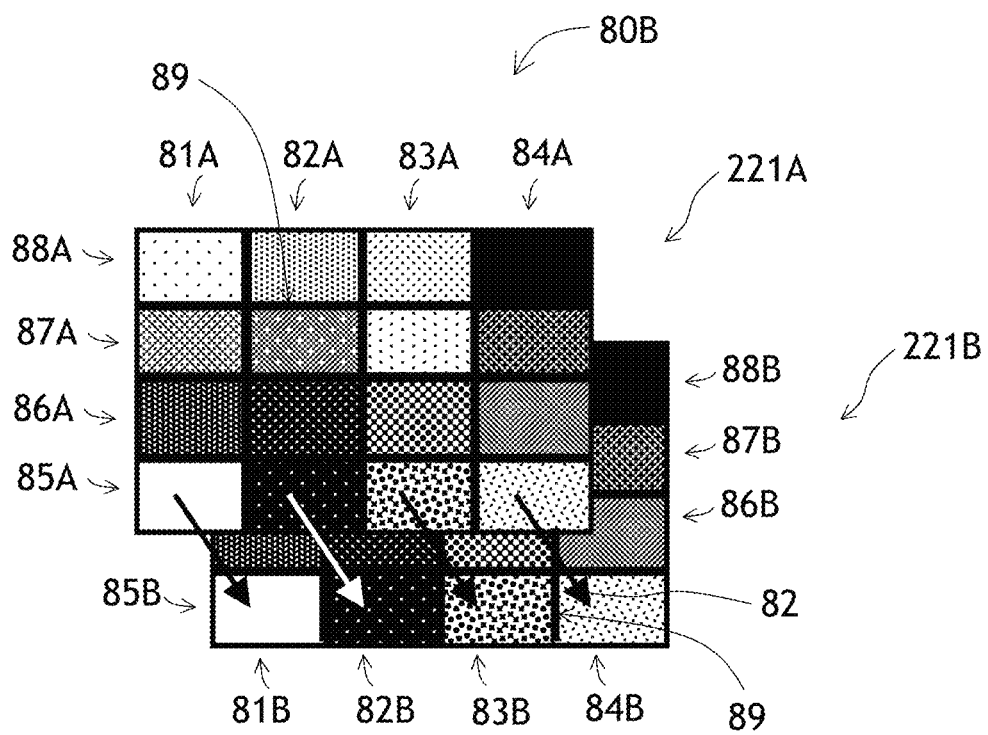

Turning to FIG. 8B, an optical assembly 80B according to an example implementation, may be a two-dimensional (2D) segmented optical filter assembly. The first 221A and second 221B segmented laterally variable bandpass optical filters of the optical assembly 80B may each include 2D arrays of the bandpass optical filter segments 81A-84A and 81B-84B. By way of illustration, the first segmented laterally variable bandpass optical filter 221A may include four one-dimensional arrays 85A, 86A, 87A, 88A arranged side by side in the second direction 25' and combined into a two-dimensional array, each such one-dimensional array 85A-88A including the bandpass optical filter segments 81A-84A having transmission center wavelengths $\lambda_T$ unique to the entire two-dimensional array and arranged side by side in the first direction 25. Similarly, the second segmented laterally variable bandpass optical filter 221B may include one-dimensional arrays 85B, 86B, 87B, 88B arranged side by side in the second direction 25' and combined into a two-dimensional array, each such one-dimensional array 85B-88B including the bandpass optical filter segments 81B-84B having a unique transmission center wavelength $\lambda_T$ and arranged side by side in the first direction 25. The transmission center wavelengths $\lambda_T$ of the bandpass optical filter segments 81A-84A and 81B-84B of the first 221A and second 221B segmented laterally variable bandpass optical filters may be mutually coordinated along the first direction 25 and along a second direction 25' perpendicular to the first direction 25 and transversal to the optical path 22 (not shown in FIGS. 8A, 8B). In one embodiment, a black grid 89 separating neighboring bandpass optical filter segments 81A-84A or 81B-84B of at least one of the first 221A and second 221B segmented laterally variable bandpass optical filters may be provided for suppressing light leakage between neighboring bandpass optical filter segments 81A-84A or 81B-84B.

Figures 8C, 8D:
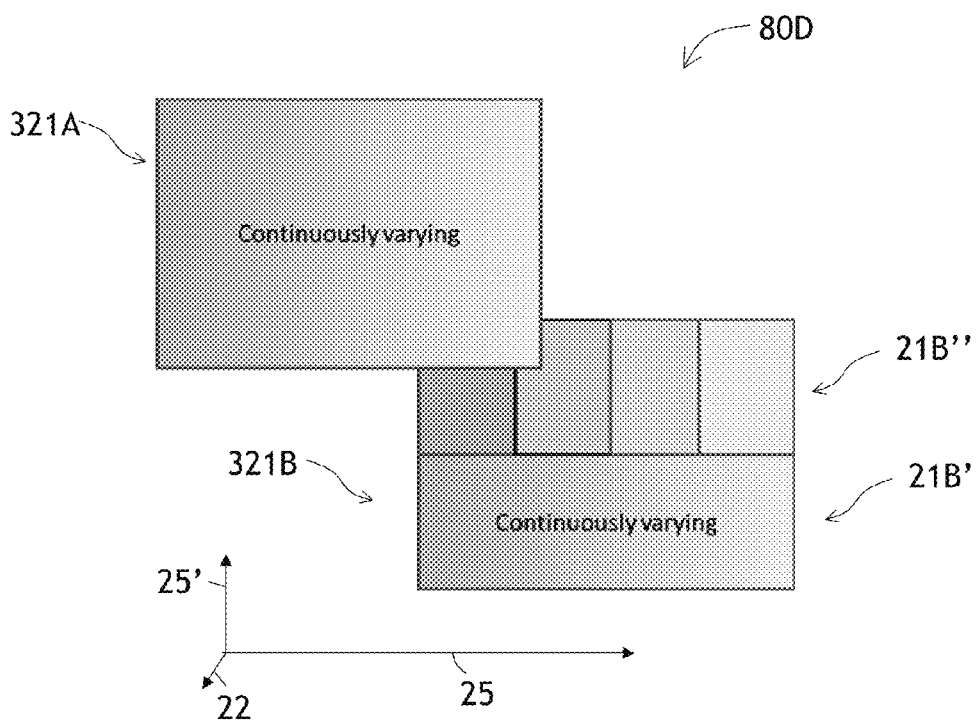

According to one aspect of the disclosure, the transmission center wavelengths $\lambda_T$ of neighboring bandpass optical filter segments 81A-84A and 81B-84B for each array 85A-88A and 85B-88B need not be successive, that is, need not be disposed in an increasing or decreasing order. The stepwise laterally variable bandpass center wavelength of the first 221A or second 221B segmented laterally variable bandpass optical filters needs not be monotonically increasing or decreasing. In fact, it may be preferable to "scramble" the transmission center wavelength $\lambda_T$, so neighboring bandpass optical filter segments 81A-84A and 81B-84B for each array 85A-88A and 85B-88B differ in the transmission center wavelength $\lambda_T$ by a magnitude larger than a "typical" wavelength increment of the transmission center wavelength $\lambda_T$. By way of a non-limiting example, referring to FIG. 8C, transmission center wavelengths $\lambda_T$ of neighboring bandpass optical filter segments 81A-84A and 81B-84B of a segmented filter 80C are shown (in nanometers) for each array 85A-88A. In FIG. 8C, the top left segment 81A of the top row 88A has the transmission center wavelength $\lambda_T$=700 nm, while its immediate neighbor to the right 82A has the transmission center wavelength $\lambda_T$=900 nm, and its immediate neighbor below 87A has the transmission center wavelength $\lambda_T$=1050 nm. The transmission center wavelengths $\lambda_T$ of the bandpass optical filter segments 81A-84A and 81B-84B of the first 221A and second 221B segmented laterally variable bandpass optical filters may be spread across a wavelength range with a constant or variable wavelength step such that the transmission center wavelengths $\lambda_T$ of the neighboring bandpass optical filter segments 81A-84A and 81B-84B of the first 221A and second 221B segmented laterally variable bandpass optical filters differ at least by an integer multiple of the constant or variable wavelength step. For instance, if the wavelength step is 25 nm, that is, the transmission center wavelength $\lambda_T$ of the bandpass optical filter segments 81A-84A and/or 81B-84B includes the values of 700 nm; 725 nm; 750 nm; and so on, the transmission center wavelengths $\lambda_T$ of the neighboring bandpass optical filter segments 81A-84A and 81B-84B of the first 221A and second 221B segmented laterally variable bandpass optical filters may differ at least by 125 nm=5*25 nm, that is, five times the wavelength step. For example, the minimum difference between the transmission center wavelengths $\lambda_T$ of the neighboring bandpass optical filter segments in each individual array 85A-88A, that is, in horizontal direction in FIG. 8C, is between the leftmost bottom bandpass optical filter segments 81A (1000 nm) and 82A (875 nm) in the bottom array 85A. All the other differences in each individual array 85A-88A in FIG. 8C, that is, in horizontal direction, are larger. The differences in vertical direction may be somewhat smaller in this example, e.g. at least 75 nm=3*25 nm, that is, three times the wavelength step. Thus, the differences in the transmission center wavelengths $\lambda_T$ of the horizontal or vertical optical filter segments 81A-84A and/or 81B-84B may be at least three times the wavelength step. The wavelength step may be variable i.e. the transmission center wavelength $\lambda_T$ of the optical filter segments 81A-84A and/or 81B-84B may include, for example, the values of 700 nm; 711 nm; 722 nm; 733 nm; and so on. The total number of the optical filter segments 81A-84A and/or 81B-84B may of course vary. The bandpass optical filter segments 81A-84A of the first 221A or second 221B segmented laterally variable bandpass optical filters may include a colored glass, an absorptive pigment, or a dye, for absorption of light at wavelengths other than wavelengths of corresponding passbands of the bandpass optical filter segments 81A-84A.

In one embodiment, the first 221A or second 221B segmented laterally variable bandpass optical filters may have a segmented portion and a continuously varying portion. For instance, referring to FIG. 8D, an upstream filter 321A of an optical assembly 80D is a continuously varying $\lambda_T$ filter, and a downstream filter 321B of the optical assembly 80D includes a continuously varying portion 21B' and a segmented portion 21B". Similarly to the optical assembly 20 of FIG. 2A, the bandpass center wavelengths of these upstream 321A and downstream 321B filters of the optical assembly 80D of FIG. 8D may vary in a mutually coordinated fashion along the first direction 25 and/or along the second direction 25'.

Figure 9:
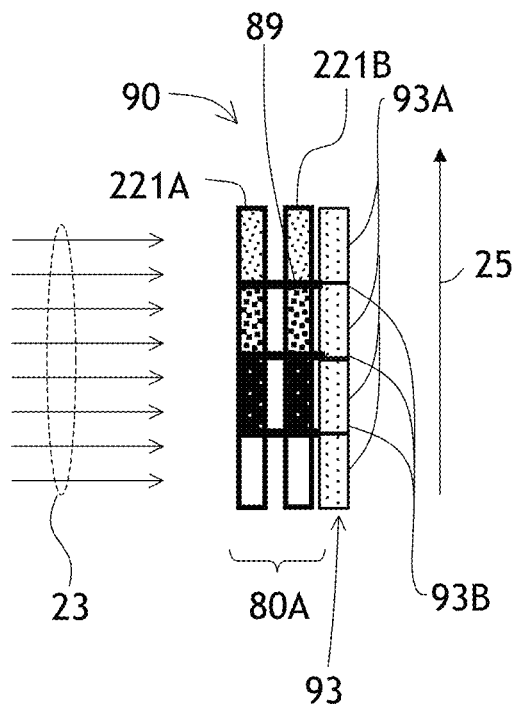
FIG. 9 is a schematic cross-sectional view of an optical assembly including the segmented first and second optical filters of FIG. 8A and a photodetector array.

Turning to FIG. 9 with further reference to FIGS. 2A and 8A, an optical spectrometer assembly 90 may include a sensor 93 optically coupled to the second laterally variable bandpass optical filter 21B of the optical assembly 20 of FIG. 2A or the second segmented laterally variable bandpass optical filter 221B of the optical assembly 80A of FIG. 8A. The sensor 93 may have a one-dimensional array of photodetectors 93A disposed along the first direction 25 separated by boundaries 93B between the individual photodetectors 93A. Thus, the photodetectors 93A may be disposed for wavelength selective detection of the signal light 23 propagated through the second segmented laterally variable bandpass optical filter 221B. For embodiments including the optical assembly 80A of FIG. 8A, the sensor 93 may have one photodetector corresponding to each segment 81B-84B. In the example implementation shown in FIG. 9, the black grid 89 may be disposed between neighboring bandpass optical filter segments 81B-82B, 82B-83B, and 83B-84B of the second segmented laterally variable bandpass optical filter 221B and along the boundaries 93B between the photodetectors 93A. In one embodiment, the black grid 89 may extend between the first 221A and second 221B segmented laterally variable bandpass optical filters, as shown.

Figure 10A:
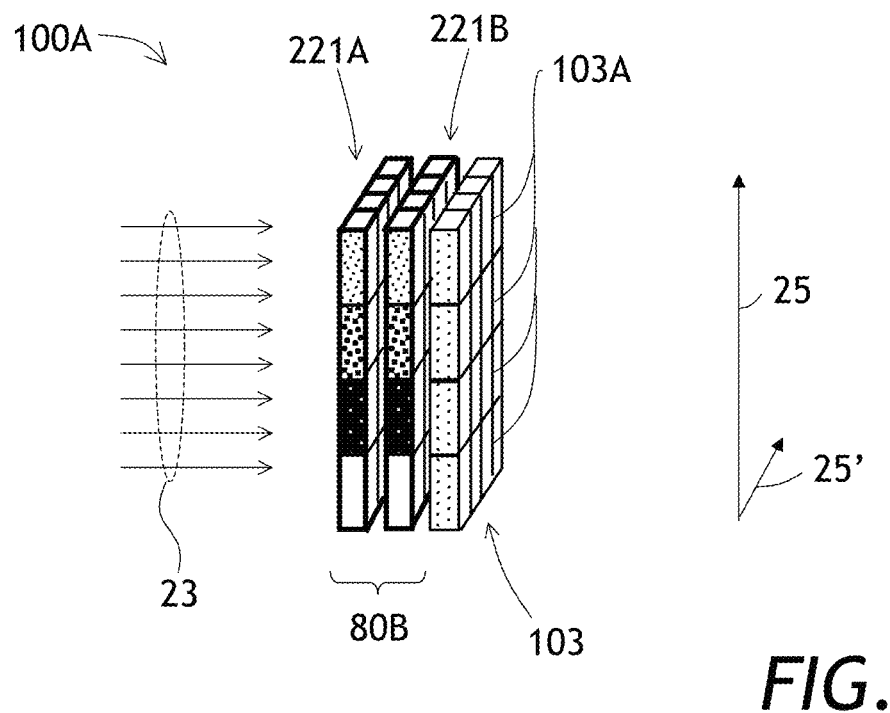
FIG. 10A is a three-dimensional view of an optical assembly comprising the segmented laterally variable optical filter of FIG. 8B and a 2D photodetector array.

Referring to FIG. 10A, an optical spectrometer assembly 100A according to an example implementation may include a sensor 103 optically coupled to the second segmented laterally variable bandpass optical filter 221B of the optical assembly 80B of FIG. 8B or the optical assembly 80D of FIG. 8D. The sensor 103 may have a two-dimensional array of photodetectors 103A optically coupled to the second segmented laterally variable bandpass optical filter 221B and having the photodetectors 103A disposed along the first direction 25 and the second direction 25', for wavelength selective detection of the signal light 23 propagated through the second segmented laterally variable bandpass optical filter 221B.

Figure 10B:
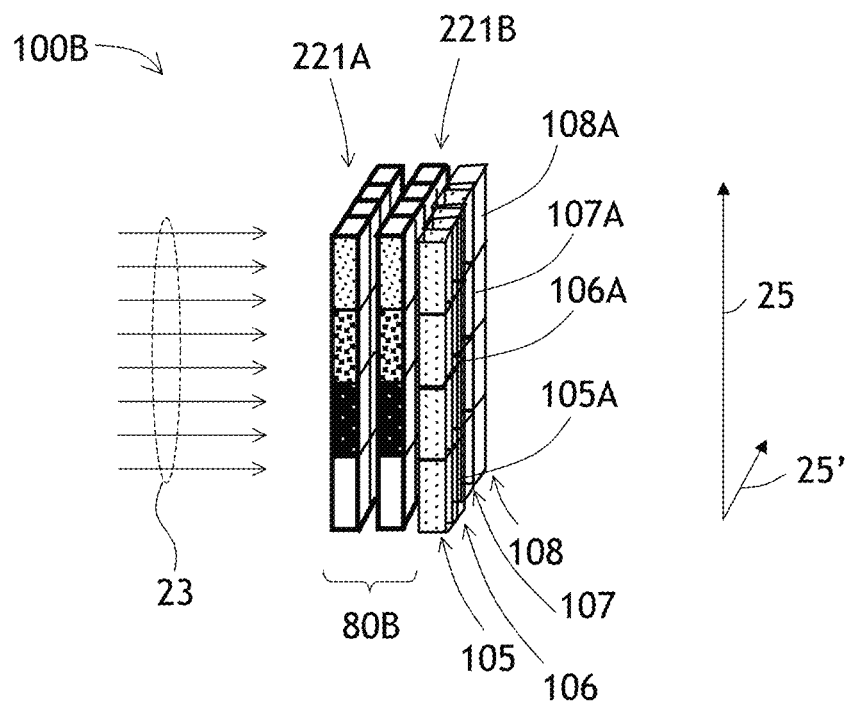
FIG. 10B is a diagram of a schematic three-dimensional view of an optical assembly comprising the segmented laterally variable optical filters of FIG. 8B and a plurality of photodetector arrays.

Turning to FIG. 10B, an optical spectrometer assembly 100B according to an example implementation may include a plurality of sensors 105, 106, 107, 108 disposed side by side along the second direction 25' and optically coupled to the second segmented laterally variable bandpass optical filter 221B of the optical assembly 80B of FIG. 8B or the optical assembly 80D of FIG. 8D. Each of the sensors 105-108 may include a photodetector array extending along the first direction 25. For instance, the first sensor 105 may include an array of photodetectors 105A extending along the first direction 25; the second sensor 106 may include an array of photodetectors 106A extending along the first direction 25; the third sensor 107 may include an array of photodetectors 107A extending along the first direction 25; and the fourth sensor 108 may include an array of photodetectors 108A extending along the first direction 25. The sensors 105-108 may be spaced apart along the second direction 25', or may be joined. Each sensor 105-108 may be optically coupled to the second segmented laterally variable bandpass optical filter 221B. Each sensor 105-108 may have a corresponding operational wavelength range, and a corresponding plurality of the bandpass optical filter segments 85B-88B optically coupled to the sensor 105-108. By way of a non-limiting example, silicon (Si) based sensor arrays may be used in a visible—near infrared range of wavelengths between 200 nm and 1100 nm, and indium gallium arsenide (InGaAs) based sensor arrays may be used in an infrared range of wavelengths between 500 nm and 2600 nm. The transmission center wavelengths $\lambda_T$ of the pluralities of the bandpass optical filter segments 85B-88B (and, accordingly, 85A-88A) may be selected to be within the operational wavelength ranges of the corresponding photodetector arrays 105-108. In this way, a multi-spectral optical spectrometer assembly may be constructed. It is further noted that the segmented filter configurations of the optical assemblies 80A-80D of FIGS. 8A-8D, and the sensor configurations of FIGS. 10A, 10B may also be used, for example, in the optical spectrometer assemblies 50 of FIG. 5, 60 of FIGS. 6A and 6B, and 70 of FIGS. 7A and 7B.

Figure 11:
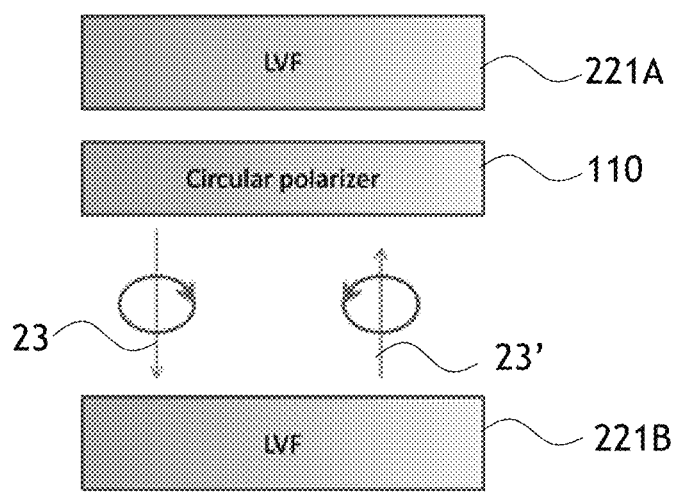
FIG. 11 is a schematic side view of an optical filter assembly including a circular polarizer.

Referring to FIG. 11, a circular polarizer 110 according to an example implementation may be disposed in the optical path 22 between the first 221A and second 221B laterally variable bandpass optical filters, for suppressing light 23' reflected from the second laterally variable bandpass optical filter 221B. The circular polarizer 110 polarizes the incoming light 23 to be in clockwise circular polarization, for example. The reflected light 23' will be counterclockwise polarized due to reversal of the direction of propagation. The reflected light 23' may be suppressed by the circular polarizer 110, i.e., an absorbing circular polarizer which removes the energy of the reflected light 23'. The circular polarizer 110 may also be disposed between the first 21A and second 21B laterally variable bandpass optical filters of the optical assembly 20 of FIG. 2, to suppress light reflected from the second laterally variable bandpass optical filter 21B.

Figure 12A:
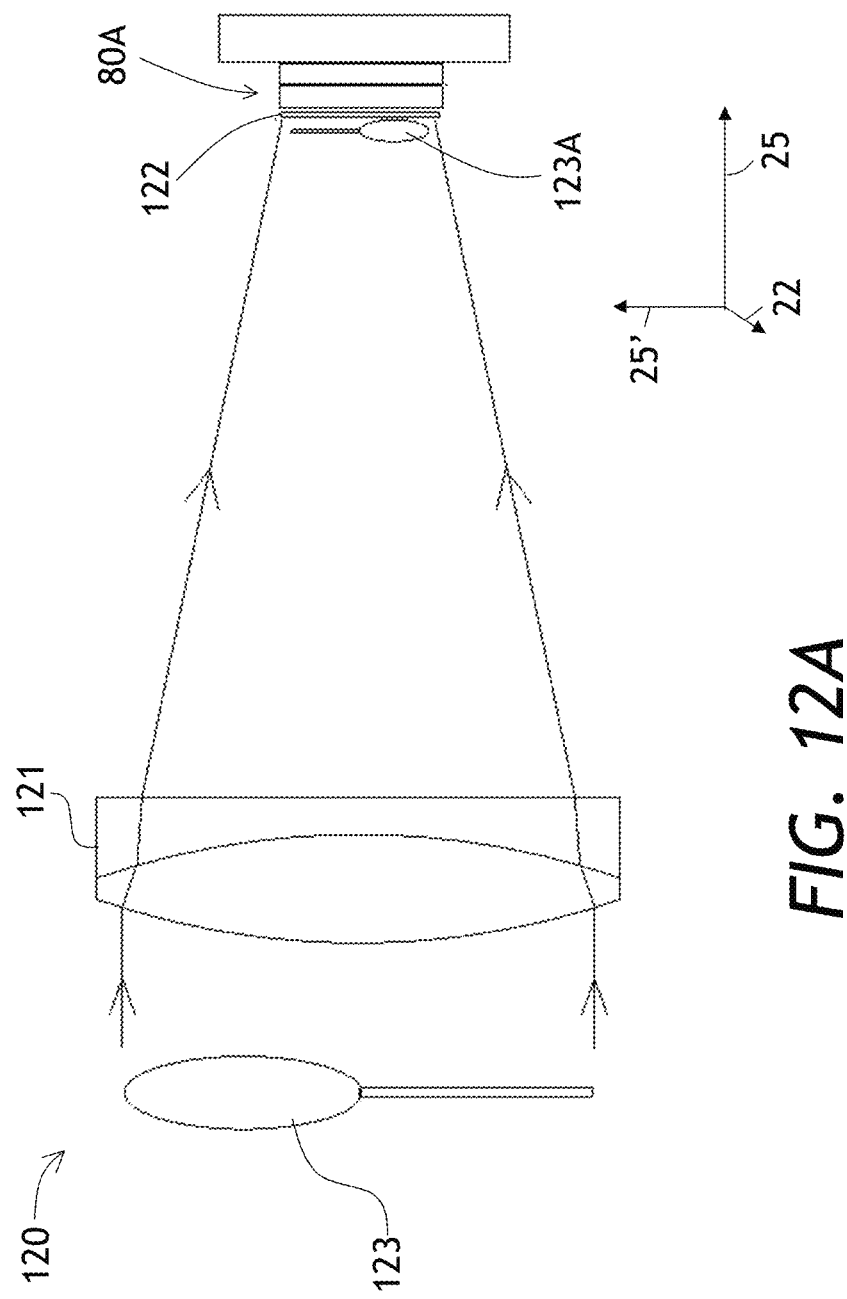
FIG. 12A is a diagram of a side cross-sectional view of an optical assembly comprising an optical objective for multi-spectral imaging.
Figure 12B:
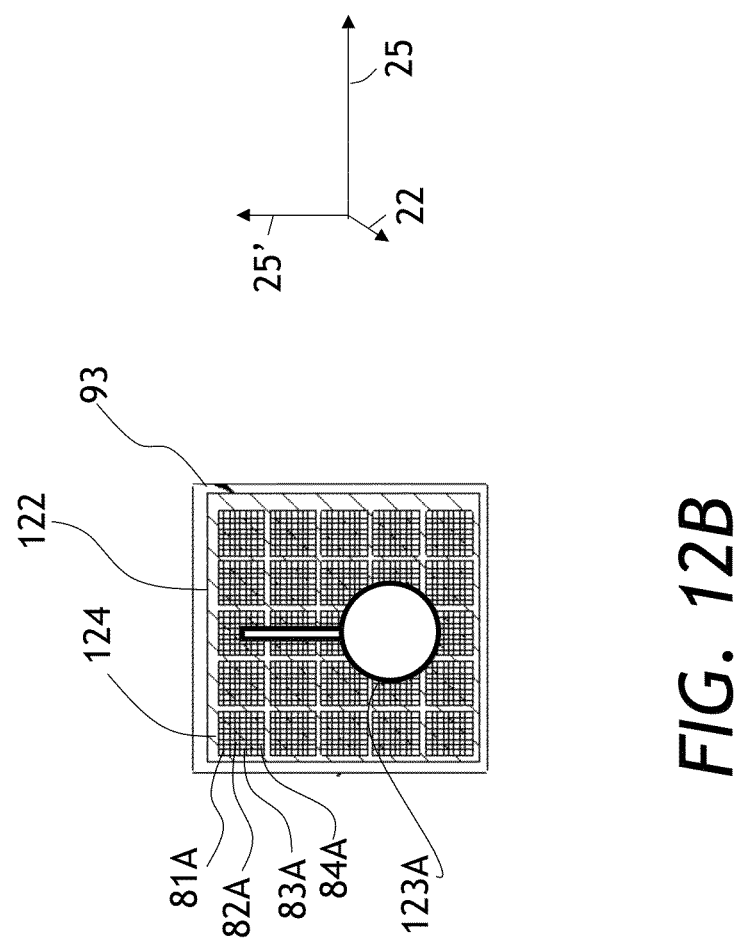
FIG. 12B is a diagram of a plan view of an image of an object overlaid onto a two-dimensional detector array of the optical assembly of FIG. 12A.

Turning now to FIGS. 12A and 12B, an imaging optical assembly 120 according to an example implantation, may include, for example, the optical assembly 80B of FIG. 2B and an objective lens 121 optically coupled to an optional diffuser 122 optically coupled to the first segmented laterally variable bandpass optical filter 221A for forming an image 123A of an object 123 on the diffuser 122 or directly on the first segmented laterally variable bandpass optical filter 221A. The first 221A and second 221B segmented laterally variable bandpass optical filters may each have the respective invariable bandpass optical filter segments 81A-84A, 81B-84B (only the segments 81A-84A of the first segmented laterally variable bandpass optical filter 221A are shown for brevity) grouped into "compound pixels" 124, each compound pixel 124 including a pre-defined set of laterally invariable bandpass optical filter segments 81A-84A, 81B-84B having pre-defined transmission center wavelengths $\lambda_T$ common to each compound pixel. This configuration may be similar to one employed in color CMOS sensors used for digital photography, only the number of the filters segments 81A-84A may be at least 5, or even at least 12. Such configurations may enable multi-spectral imaging of the object 123.

The sensor 103 (FIG. 10A) may be optically coupled to the second segmented laterally variable bandpass optical filter 221B (FIGS. 12A, 12B). The sensor 103 may include photodetectors 103A disposed along the first direction 25 and the second direction 25', for wavelength selective detection of the signal light 23 propagated through the first segmented laterally variable bandpass optical filter 221A and the second segmented laterally variable bandpass optical filter 221B. The diffuser 122, when used, may spread the image 123A formed by the objective lens 121 on the first segmented laterally variable bandpass optical filter 221A. The objective lens 121 may be replaced with another image-forming optical element such as a concave mirror, for example. The 2D sensor 103 may be replaced with the 1D sensor 93 of FIG. 9 or with the plurality of sensors 105-108 of FIG. 10B.

Figure 13:
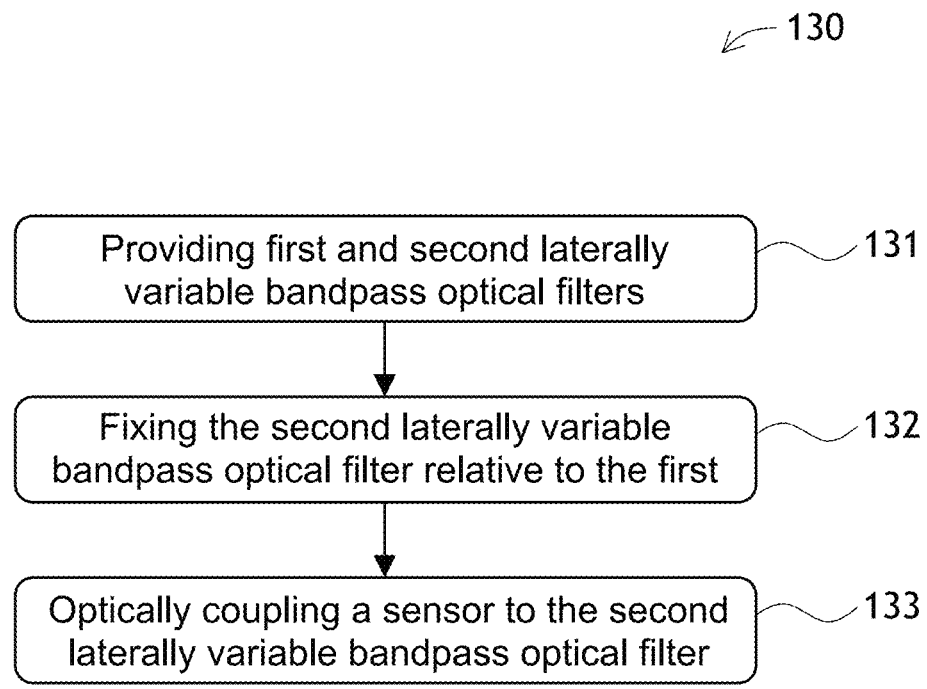
FIGS. 13, 14, and 15 are flow charts of methods of manufacture of various embodiments of optical spectrometer assemblies of the disclosure.

Referring to FIG. 13, a method 130 of making an optical spectrometer assembly of the disclosure may include a step 131 of providing the first laterally variable bandpass optical filter 21A and a second laterally variable bandpass optical filter 21B. In a step 132, the second laterally variable bandpass optical filter 21B may be fixed at the distance L from the first laterally variable bandpass optical filter 21A in the optical path 22 downstream of the first laterally variable bandpass optical filter 21A. Finally in a step 133, the sensor 43 may be optically coupled to the second laterally variable bandpass optical filter 21B. As explained above, the sensor 43 may include the photodetectors 43A disposed along the first direction 25 for wavelength selective detection of the signal light 23 propagated along the optical path 22 through the second laterally variable bandpass optical filter 21B.

Figure 14:
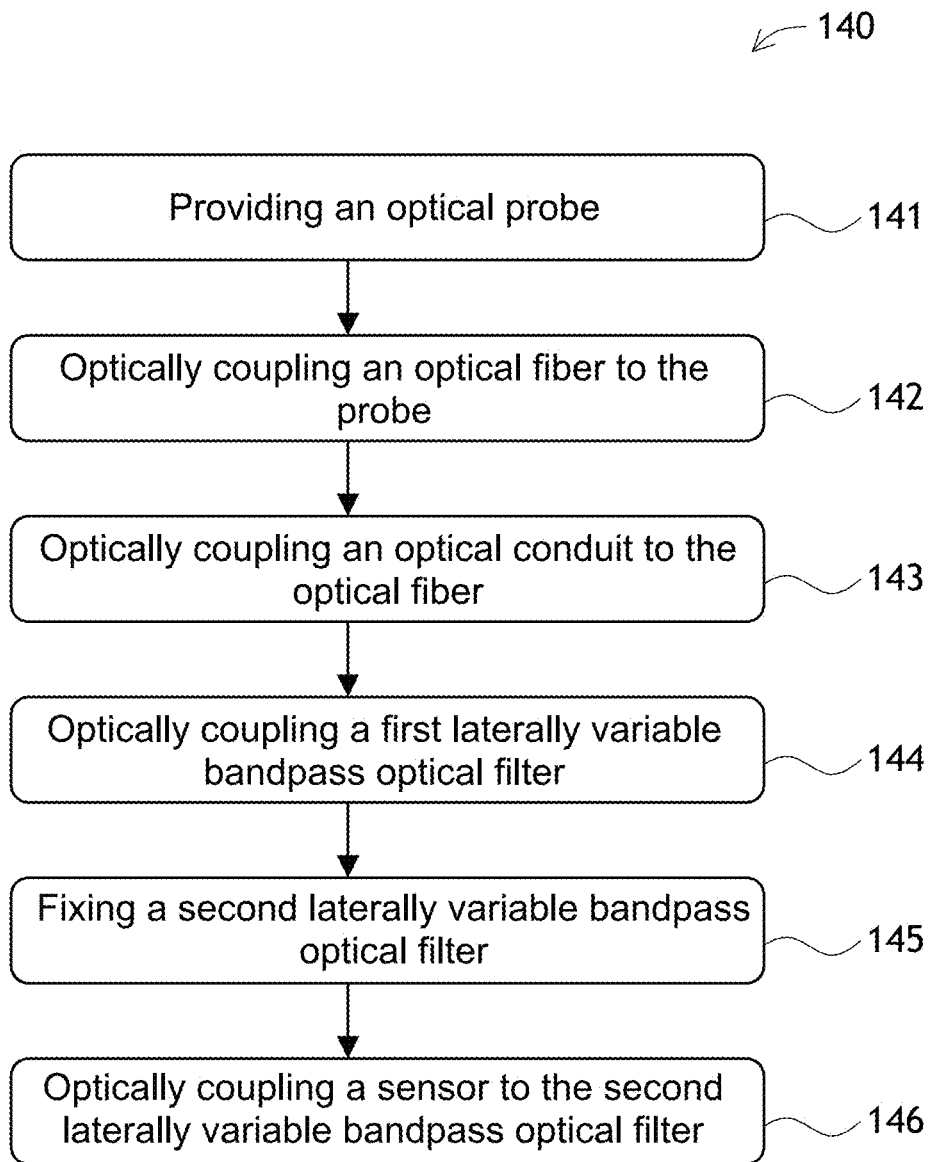

Turning to FIG. 14, a method 140 of making the optical spectrometer assembly 50 of FIG. 5 may include a step 141 of providing the optical probe 52 for collecting the signal light 23 emanating from the sample 51 when the sample 51 is illuminated with the illuminating light 53. In a step 142, the first end 41A of the optical fiber 41 may be optically coupled to the probe 52 for receiving the signal light 23 collected by the optical probe 52 and propagating the signal light 23 in the optical fiber 41 towards its second end 41B. In a next step 143, the first surface 42A of the optical conduit 42 may be optically coupled to the second end 41B of the optical fiber 41 for receiving the signal light 23 propagated to the second end 41B of the optical fiber 41 for propagating in the optical conduit 42 towards its second surface 42B. In a next step 144, the first laterally variable bandpass optical filter 21A may be optically coupled to the second surface 42B of the optical conduit 42 for receiving the signal light 23 propagated in the optical conduit 42.

In a following step 145, the second laterally variable bandpass optical filter 21B may be fixed at the distance L from the first laterally variable bandpass optical filter 21A in the optical path 22 of the signal light 23 downstream of the first laterally variable bandpass optical filter 21A. Finally in a step 146, the sensor 43 may be optically coupled to the second laterally variable bandpass optical filter 21B. A one-dimensional or two-dimensional detector array may be used in place of the sensor 43.

Figure 15:
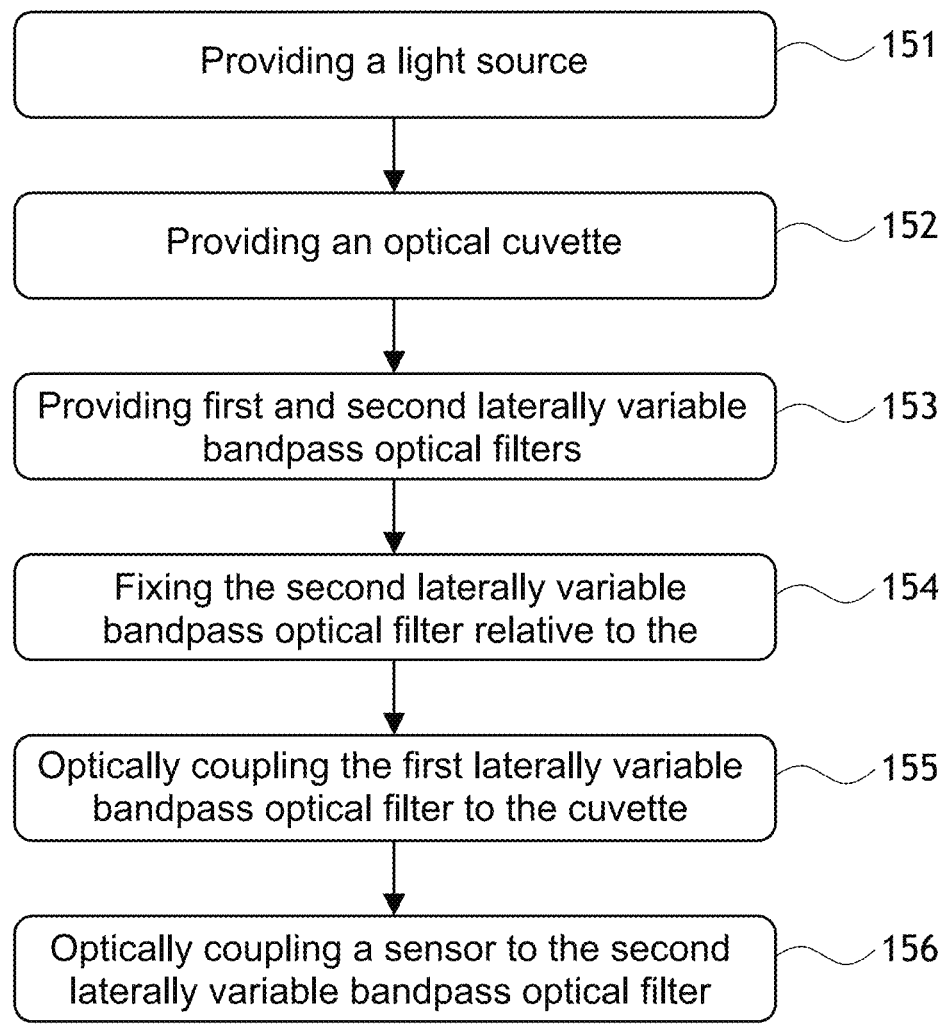

Referring to FIG. 15, a method 150 of making the optical spectrometer assembly 60 may include a step 151 of providing the light source 61 for providing the illuminating light 53. In a step 152, the optical cuvette 62 may be provided. In a step 153, the first 21A and second 21B laterally variable bandpass optical filters may be provided. In a step 154, the second laterally variable bandpass optical filter 21B may be fixed at the distance L from the first laterally variable bandpass optical filter 21A in the optical path of the signal light 53 downstream of the first laterally variable bandpass optical filter 21A. In a step 155, the first laterally variable bandpass optical filter 21A may be optically coupled to the transparent sidewall 64 for receiving the signal light 53. Finally in a step 156, the sensor 43 may be optically coupled to the second laterally variable bandpass optical filter 21B. A one-dimensional or two-dimensional detector array may be used in place of the sensor 43. In the methods 130, 140, and 150, segmented laterally variable bandpass optical filters 221A and 221B may be used instead of the laterally variable bandpass optical filters 21A and 21B.

An optical filter and spectrometer may involve the processing of input data and the generation of output data. This input data processing and output data generation may be implemented in hardware and/or software. For example, specific electronic components may be employed in a processor, module, or similar related circuitry for implementing the functions associated with providing an optical filter and/or a spectrometer in accordance with the various example implementations described above. Alternatively, one or more processors operating in accordance with instructions may implement the functions associated with the exemplary implementations described above. Such instructions may be stored on one or more processor readable storage media (e.g., a magnetic disk or other storage medium), or be transmitted to one or more processors via one or more signals embodied in one or more carrier waves.

The present disclosure is not to be limited in scope by the specific example implementations described herein. Indeed, other implementations and modifications, in addition to those described herein, will be apparent to those of ordinary skill in the art from the foregoing description and accompanying drawings. Thus, such other implementation and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. An optical assembly comprising:
a first laterally variable bandpass optical filter in an optical path of signal light; and
a second laterally variable bandpass optical filter fixed at a first distance from the first laterally variable bandpass optical filter in the optical path downstream of the first laterally variable bandpass optical filter,
wherein the first laterally variable bandpass optical filter has a first bandpass center wavelength,
wherein the second laterally variable bandpass optical filter has a second bandpass center wavelength,
wherein the first bandpass center wavelength and the second bandpass center wavelength vary in a mutually coordinated fashion along a first direction transversal to the optical path, and
wherein the first bandpass center wavelength and the second bandpass center wavelength have a substantially identical dependence on distance along the first direction.

2. The optical assembly of claim 1, wherein the first bandpass center wavelength and the second bandpass center wavelength monotonically increase in the first direction.

3. The optical assembly of claim 1, further comprising:
an optical fiber having a first end and a second end; and
an optical conduit having a first surface and a second surface,
wherein the first surface of the optical conduit is optically coupled to the second end of the optical fiber, and
wherein the second surface of the optical conduit is optically coupled to the first laterally variable bandpass optical filter.

4. The optical assembly of claim 3, wherein the optical conduit further comprises a third surface disposed in an optical path between the first surface and the second surface, for receiving the signal light from the first surface and reflecting the signal light towards the second surface.

5. The optical assembly of claim 3,
wherein in operation, a portion of the signal light is reflected from the first laterally variable bandpass optical filter, and
wherein the optical conduit comprises a reflective wall for redirecting at least a portion of the reflected light portion back to the first laterally variable bandpass optical filter.

6. The optical assembly of claim 3,
wherein the optical conduit comprises a slab of homogeneous transparent material defined by a plurality of external surfaces comprising the first surface and the second surface, and
wherein the slab is configured for unconstrained propagation of the signal light therein.

7. The optical assembly of claim 1, further comprising:
a circular polarizer disposed in the optical path between the first and second laterally variable bandpass optical filters, for suppressing light reflected from the second laterally variable bandpass optical filter in a direction towards the first laterally variable bandpass optical filter.

8. The optical assembly of claim 1, further comprising:
a photodetector array optically coupled to the second laterally variable bandpass optical filter and comprising photodetectors disposed along the first direction for wavelength selective detection of signal light propagated through the second laterally variable bandpass optical filter.

9. An optical assembly comprising:
an optical probe for collecting signal light emanating from a sample when the sample is illuminated with illuminating light;
an optical fiber having a first end and a second end,
wherein the first end is optically coupled to the optical probe for receiving the signal light collected by the optical probe and propagating the signal light to the second end;
an optical conduit having a first surface and a second surface,
wherein the first surface of the optical conduit is optically coupled to the second end of the optical fiber for receiving the signal light propagated to the second end of the optical fiber, for propagating in the optical conduit;
a first laterally variable bandpass optical filter optically coupled to the second surface of the optical conduit for receiving the signal light propagated in the optical conduit; and
a second laterally variable bandpass optical filter fixed at a first distance from the first laterally variable bandpass optical filter and downstream thereof in an optical path of the signal light,
wherein the first laterally variable bandpass optical filter has a first bandpass center wavelength, and the second laterally variable bandpass optical filter has a second bandpass center wavelength,
wherein the first bandpass center wavelength and the second bandpass center wavelength vary in a mutually coordinated fashion along a first direction transversal to the optical path,
wherein at least one of the first laterally variable bandpass optical filter or the second laterally variable bandpass optical filter comprises a plurality of bandpass optical filter segments arranged side by side, and
wherein each bandpass optical filter segment has a laterally invariable transmission center wavelength different from a transmission center wavelength of an immediate neighboring bandpass optical filter segment.

10. The optical assembly of claim 9,
wherein the optical probe comprises a relay lightpipe comprising a proximal end and a distal end, wherein the distal end is configured for contacting or inserting into the sample, thereby collecting the signal light emanating from the sample, and wherein the relay lightpipe is further configured for unconstrained propagation of the signal light in bulk of the relay lightpipe from the proximal end to the distal end.

11. The optical assembly of claim 10, wherein the distal end of the relay lightpipe comprises a slanted optical surface.

12. The optical assembly of claim 9, wherein the optical probe comprises a transmission cuvette for holding the sample in fluid or granular form.

13. The optical assembly of claim 9, further comprising:
a photodetector array optically coupled to the second laterally variable bandpass optical filter and comprising photodetectors disposed along the first direction for wavelength selective detection of the signal light propagated through the second laterally variable bandpass optical filter.

14. The optical assembly of claim 9, further comprising:
a two-dimensional photodetector array optically coupled to the second laterally variable bandpass optical filter and comprising photodetectors disposed along the first direction and a second direction, for wavelength selective detection of the signal light propagated through the second laterally variable bandpass optical filter.

15. A method of making an optical spectrometer assembly, the method comprising:
providing a first laterally variable bandpass optical filter having a first bandpass center wavelength, and a second laterally variable bandpass optical filter having a second bandpass center wavelength;
fixing the second laterally variable bandpass optical filter at a first distance from the first laterally variable bandpass optical filter in an optical path downstream of the first laterally variable bandpass optical filter,
wherein the first bandpass center wavelength and the second bandpass center wavelength vary in a mutually coordinated fashion along a first direction transversal to the optical path; and
optically coupling a sensor to the second laterally variable bandpass optical filter,
wherein the sensor comprises photodetectors disposed along the first direction for wavelength selective detection of signal light propagated along the optical path through the second laterally variable bandpass optical filter, and
wherein the first bandpass center wavelength and the second bandpass center wavelength have a substantially identical dependence on distance along the first direction.

16. The method of claim 15, further comprising:
optically coupling a distal end of an optical probe with a sample.

17. The method of claim 15, wherein the first bandpass center wavelength and the second bandpass center wavelength monotonically increase in the first direction.

18. The method of claim 15,
optically coupling a first end of an optical fiber to an optical probe; and
optically coupling a first surface of an optical conduit to a second end of the optical fiber.

19. The method of claim 18, further comprising:
optically coupling a second surface of the optical conduit to the first laterally variable bandpass optical filter.

20. The method of claim 19, wherein the optical conduit further comprises a third surface disposed in an optical path between the first surface and the second surface, for receiving the signal light from the first surface and reflecting the signal light towards the second surface.

21. The method of claim 18,
wherein in operation, a portion of the signal light is reflected from the first laterally variable bandpass optical filter, and
wherein the optical conduit comprises a reflective wall for redirecting at least a portion of the reflected light portion back to the first laterally variable bandpass optical filter.

22. The method of claim 18, wherein the optical conduit comprises a slab of homogeneous transparent material defined by a plurality of external surfaces comprising the first surface and the second surface.

23. A method of making an optical spectrometer assembly, the method comprising:
providing an optical probe for collecting signal light emanating from a sample when the sample is illuminated with illuminating light;
optically coupling a first end of an optical fiber to the optical probe for receiving the signal light collected by the optical probe and propagating the signal light in the optical fiber towards a second end thereof;
optically coupling a first surface of an optical conduit to the second end of the optical fiber for receiving the signal light propagated to the second end of the optical fiber, for propagating in the optical conduit towards a second surface thereof;
optically coupling a first laterally variable bandpass optical filter having a first bandpass center wavelength to the second surface of the optical conduit for receiving the signal light propagated in the optical conduit;
fixing a second laterally variable bandpass optical filter having a second bandpass center wavelength at a first distance from the first laterally variable bandpass optical filter in an optical path of the signal light, downstream of the first laterally variable bandpass optical filter,
wherein the first bandpass center wavelength and the second bandpass center wavelength vary in a mutually coordinated fashion along a first direction transversal to the optical path; and
optically coupling a sensor to the second laterally variable bandpass optical filter,
wherein the sensor comprises photodetectors disposed along the first direction for wavelength selective detection of the signal light propagated through the second laterally variable bandpass optical filter,
wherein at least one of the first laterally variable bandpass optical filter or the second laterally variable bandpass optical filter comprises a plurality of bandpass optical filter segments arranged side by side, and
wherein each bandpass optical filter segment has a laterally invariable transmission center wavelength different from a transmission center wavelength of an immediate neighboring bandpass optical filter segment.

24. The method of claim 23, further comprising:
optically coupling a distal end of the optical probe with the sample.

25. The method of claim 23, wherein the optical probe comprises a relay lightpipe comprising a proximal end and a distal end.

26. The method of claim 25, wherein the distal end is configured for contacting or inserting into the sample, thereby collecting the signal light emanating from the sample.

27. The method of claim 25, wherein the relay lightpipe is configured for unconstrained propagation of the signal light in bulk of the relay lightpipe from the proximal end to the distal end.

28. The method of claim 25, wherein the distal end of the relay lightpipe comprises a slanted optical surface.

29. The method of claim 23, wherein the optical probe comprises a transmission cuvette for holding the sample in fluid or granular form.

30. The method of claim 23, further comprising:
   optically coupling a photodetector array to the second laterally variable bandpass optical filter.

31. The method of claim 30, wherein the photodetector array comprises photodetectors disposed along the first direction for wavelength selective detection of the signal light propagated through the second laterally variable bandpass optical filter.

32. The method of claim 30, wherein the photodetector array comprises a two-dimensional photodetector array that includes photodetectors disposed along the first direction and a second direction, for wavelength selective detection of the signal light propagated through the second laterally variable bandpass optical filter.

* * * * *